United States Patent
Hanzawa et al.

(10) Patent No.: US 11,933,961 B2
(45) Date of Patent: Mar. 19, 2024

(54) STEREOSCOPIC VISION ENDOSCOPE OBJECTIVE OPTICAL SYSTEM AND ENDOSCOPE USING THE SAME

(71) Applicant: OLYMPUS CORPORATION, Hachioji (JP)

(72) Inventors: Toyoharu Hanzawa, Mitaka (JP); Takeshi Suga, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 808 days.

(21) Appl. No.: 17/061,447

(22) Filed: Oct. 1, 2020

(65) Prior Publication Data

US 2021/0141209 A1    May 13, 2021

Related U.S. Application Data

(63) Continuation of application No. PCT/JP2019/006445, filed on Feb. 21, 2019.

(30) Foreign Application Priority Data

Apr. 11, 2018    (JP) .................................. 2018-076034

(51) Int. Cl.
*G02B 23/00* (2006.01)
*A61B 1/00* (2006.01)
(Continued)

(52) U.S. Cl.
CPC ...... *G02B 23/2415* (2013.01); *A61B 1/00096* (2013.01); *A61B 1/00188* (2013.01);
(Continued)

(58) Field of Classification Search
CPC ... G02B 9/34; G02B 9/58; G02B 9/60; G02B 9/62; G02B 9/64; G02B 13/004;
(Continued)

(56) References Cited

U.S. PATENT DOCUMENTS 9,706,906 B2    7/2017  Namii et al.
10,088,665 B2   10/2018 Zhao et al.
(Continued)

FOREIGN PATENT DOCUMENTS

JP    5945649 B2       6/2016
JP    2016527566 A     9/2016
(Continued)

OTHER PUBLICATIONS

Japanese Office Action (and English language translation thereof) dated Oct. 6, 2021 issued in Japanese Application No. 2020-513100.
(Continued)

*Primary Examiner* — James C. Jones
*Assistant Examiner* — Henry Duong
(74) *Attorney, Agent, or Firm* — Holtz, Holtz & Volek PC

(57) ABSTRACT

A stereoscopic vision endoscope objective optical system includes, in order from an object side, a first lens group having a negative refractive power, a second lens group having a positive refractive power, and a rear-side lens group having a positive refractive power. The rear-side lens group includes a first rear group and a second rear group. The first lens group and the second lens group are disposed so that an optical axis of the second lens group coincides with an optical axis of the first lens group. The optical axis of the first lens group is located between an optical axis of the first rear group and an optical axis of the second rear group. Each of the first rear group and the second rear group includes a first sub group, an aperture stop, and a second sub group, and the first sub group includes a negative lens.

9 Claims, 11 Drawing Sheets

(51) Int. Cl.
*G02B 9/34* (2006.01)
*G02B 13/18* (2006.01)
*G02B 23/24* (2006.01)

(52) U.S. Cl.
CPC ............ *A61B 1/00193* (2013.01); *G02B 9/34* (2013.01); *G02B 13/18* (2013.01)

(58) Field of Classification Search
CPC .............. G02B 13/0045; G02B 13/005; G02B 23/2415; G02B 13/18; G02B 23/243; G03B 30/00; A61B 1/00096; A61B 1/00188; A61B 1/00193
USPC ......................................................... 359/781
See application file for complete search history.

(56) References Cited

U.S. PATENT DOCUMENTS

2016/0154231 A1   6/2016   Zhao et al.
2016/0338576 A1*  11/2016  Namii ................. G02B 23/2407
2017/0293129 A1*  10/2017  Hatakeyama ........ G02B 21/025
2018/0095262 A1   4/2018   Fukushima
2020/0192077 A1   6/2020   Hanzawa et al.

FOREIGN PATENT DOCUMENTS

JP       6072381 B1    1/2017
WO    2016006505 A1    1/2016
WO    2017017854 A1    2/2017

OTHER PUBLICATIONS

Japanese Office Action (and English language translation thereof) dated Sep. 1, 2021 issued in counterpart Japanese Application No. 2020-513100.
International Search Report (ISR) (and English language translation thereof) dated May 21, 2019, issued in International Application No. PCT/JP2019/006445.
Written Opinion dated May 21, 2019, issued in International Application No. PCT/JP2019/006445.
International Preliminary Report on Patentability (IPRP) (and English language translation thereof) dated Oct. 22, 2020 issued in International Application No. PCT/JP2019/006445.

* cited by examiner

STEREOSCOPIC VISION ENDOSCOPE OBJECTIVE OPTICAL SYSTEM AND ENDOSCOPE USING THE SAME

CROSS-REFERENCE TO RELATED APPLICATION

The present application is a continuation application of PCT/JP2019/006445 filed on Feb. 21, 2019, which is based upon and claims the benefit of priority from Japanese Patent Application No. 2018-076034 filed on Apr. 11, 2018; the entire contents of which are incorporated herein by reference.

BACKGROUND

Technical Field

The present disclosure relates to a stereoscopic vision endoscope objective optical system and an endoscope using the same.

Description of the Related Art

In an observation using an endoscope, magnified observation in which a stereoscopic structure of a tissue can be figured out in further detail has been considered to be effective. In an optical system for magnified observation, by moving a position of an object point which is focused, from a far point to a near point, it is possible to have a magnified display of a tissue.

In a range in which the focusing is possible (hereinafter, referred to as the 'focusing range'), a position of an object point farthest from the optical system is a far point, and a position of the object point nearest to the optical system is a near point. Moreover, a near-point observation is an observation in a state of having focused to the object at the near point and a far-point observation is an observation in a state of having focused to the object at the far point.

In the far-point observation, an ability to observe a wide range is sought. Whereas, in the near-point observation, an ability to acquire stereoscopic information of the object is sought.

It is possible to obtain the stereoscopic information by carrying out a stereoscopic vision. In the stereoscopic vision, a pair of images having a parallax is used. The pair of images having a parallax is acquired from a pair of optical images having the parallax. It is possible to capture the pair of optical images having the parallax by disposing a pair of optical systems in parallel.

Optical systems which form a pair of optical images are disclosed in Japanese Patent No. 6072381 Publication, and Japanese Patent No. 5945649 Publication.

In Japanese Patent No. 6072381 Publication, an image forming optical system which includes a first negative lens group having a negative refractive power, a first positive lens group having a positive refractive power, and a second positive lens group having a positive refractive power has been disclosed. The first negative lens group and the first positive lens group are disposed along a common central axis, and the second positive lens group is disposed side-by-side in a parallax direction with a common central shaft interposed in between.

In Japanese Patent No. 5945649 Publication, an endoscope objective optical system which includes a first lens group having a negative refractive power, a second lens group having a positive refractive power, and a pair of third lens groups has been disclosed. The pair of third lens groups is disposed in parallel with each other in a parallax direction.

SUMMARY

A stereoscopic vision endoscope objective optical system according to at least some embodiments of the present disclosure includes, in order from an object side:
a first lens group having a negative refractive power,
a second lens group having a positive refractive power, and
a rear-side lens group having a positive refractive power, wherein
the rear-side lens group includes a first rear group and a second rear group,
the first lens group and the second lens group are disposed so that an optical axis of the second lens group coincides with an optical axis of the first lens group,
the optical axis of the first lens group is located between an optical axis of the first rear group and an optical axis of the second rear group,
each of the first rear group and the second rear group includes a first sub group, an aperture stop, and a second sub group,
the first sub group includes a negative lens, and
following conditional expression (1) is satisfied:

$$0 < -f21n/fSUB \leq 3 \tag{1}$$

where,
f21n denotes a focal length of the negative lens in the first sub group, and
fSUB denotes a focal length of the first rear group or a focal length of the second rear group.

Moreover, an endoscope according to at least some embodiments of the present disclosure includes:
a stereoscopic vision endoscope objective optical system, and
an image sensor which captures an optical image formed by the stereoscopic vision endoscope objective optical system.

DETAILED DESCRIPTION

Figure 1A:
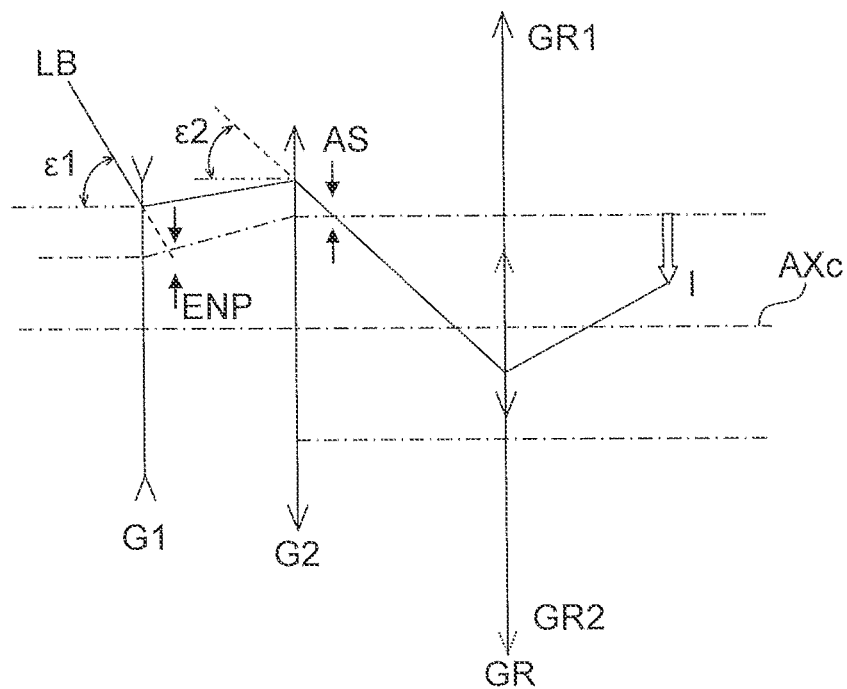
FIG. 1A and FIG. 1B are diagrams showing how an image of off-axis light is formed.

Reasons for adopting such arrangements and effects thereof in a stereoscopic vision endoscope objective optical system and an endoscope using the same according to the present embodiment, will be described below by referring to the accompanying diagrams. However, the present disclosure is not restricted to the following embodiment. A positive lens described below includes a single lens having a positive refractive power and a cemented lens having a positive refractive power. A negative lens includes a single lens having a negative refractive power and a cemented lens having a negative refractive power.

A stereoscopic vision endoscope objective optical system of the present embodiment includes, in order from an object side, a first lens group having a negative refractive power, a second lens group having a positive refractive power, and a rear-side lens group having a positive refractive power, wherein the rear-side lens group includes a first rear group and a second rear group, the first lens group and the second lens group are disposed so that an optical axis of the second lens group coincides with an optical axis of the first lens group, the optical axis of the first lens group, an optical axis of the first rear group, and an optical axis of the second rear group are located on the same plane, the optical axis of the first lens group is located between the optical axis of the first rear group and the optical axis of the second rear group, each of the first rear group and the second rear group includes a first sub group, an aperture stop, and a second sub group, the first sub group includes a negative lens, and following conditional expression (1) is satisfied:

$$0 < -f21n/fSUB \leq 3 \quad (1)$$

where, f21n denotes a focal length of the negative lens in the first sub group, and fSUB denotes a focal length of the first rear group or a focal length of the second rear group.

The stereoscopic vision endoscope objective optical system of the present embodiment includes, in order from the object side, the first lens group having a negative refractive power, the second lens group having a positive refractive power, and the rear-side lens group having a positive refractive power. The first lens group and the second lens group are disposed so that the optical axis of the second lens group coincides with the optical axis of the first lens group.

The optical axis of the first lens group, the optical axis of the first rear group, and the optical axis of the second rear group are located on the same plane. The optical axis of the first lens group is located between the optical axis of the first rear group and the optical axis of the second rear group. Accordingly, the first rear group and the second rear group are disposed in parallel.

The first rear group and the second rear group are the same optical systems. Each of the first rear group and the second rear group includes the first sub group, the aperture stop, and the second sub group. The first sub group includes the negative lens.

Accordingly, in the stereoscopic vision endoscope objective optical system of the present embodiment, it is possible to secure a wide angle of view and an appropriate stereoscopic effect, and to realize size reduction of the optical system. These points will be described below.

Figure 1B:
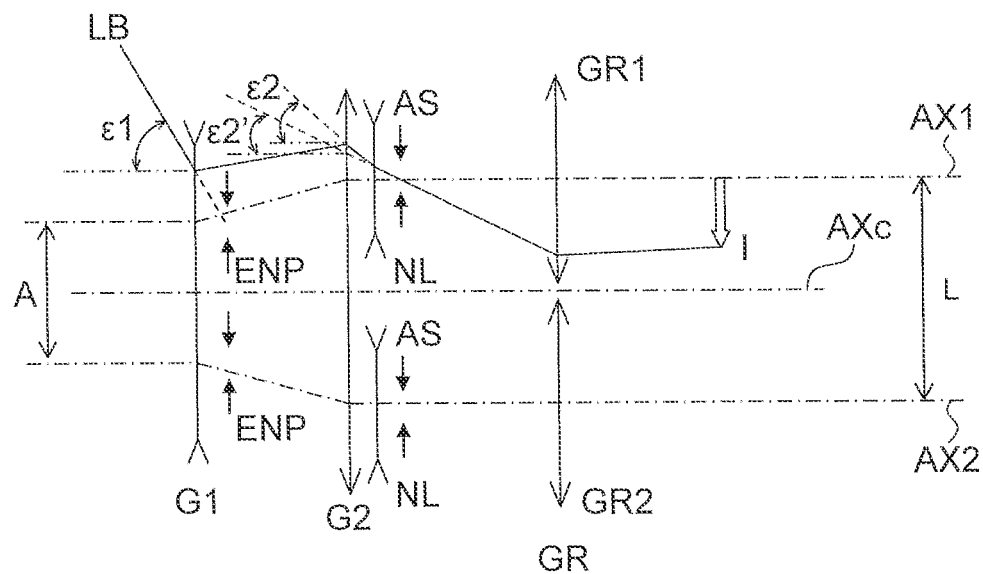

FIG. 1A and FIG. 1B are diagrams showing how an image of off-axis light is formed. FIG. 1A is a diagram showing how an image of off-axis light is formed in a conventional optical system, and FIG. 1B is a diagram showing how an image of off-axis light is formed in the stereoscopic vision endoscope objective optical system of the present embodiment. In FIG. 1A and FIG. 1B, lenses are displayed by a simplified diagram.

As shown in FIG. 1A and FIG. 1B, the optical systems include, in order from an object side, a first lens group G1 having a negative refractive power and a second lens group G2 having a positive refractive power. By making such arrangement, it is possible to make wide an angle of view of the optical system.

In an optical system with a wide angle of view, an angle ε1 of an off-axis principal light ray LB incident on a first lens group is large. In this case, when an attempt is made to secure an appropriate stereoscopic effect, in the conventional optical system, an angle ε2 of an off-axis principal light ray incident on a rear-side lens group GR becomes large. Consequently, a light-beam diameter in the rear-side lens group GR becomes large.

In the rear-side lens group GR, a lens group GR1 and a lens group GR2 are disposed in parallel. As the light-beam diameter in the rear-side lens group G becomes large, a lens diameter becomes large in each of the lens group GR1 and the lens group GR2. Consequently, the lens group GR1 and the lens group GR2 make contact.

In order that the lens group GR1 and the lens group GR2 do not make contact, a distance between the lens group GR1 and the lens group GR2 is to be widened or a lens diameter in each of the lens group GR1 and the lens group GR2 is to be made small.

However, when the distance between the lens group GR1 and the lens group GR2 is widened, the optical system becomes large. When the lens diameter is made small in each of the lens group GR1 and the lens group GR2, an effective aperture becomes small. Consequently, the angle of view becomes narrow.

Whereas, in the stereoscopic vision endoscope objective optical system of the present embodiment, a negative lens NL is disposed in a rear-side lens group GR. The negative lens GR, on the object side, is disposed near the second lens group G2. An aperture stop AS is disposed on an image side of the negative lens NL.

By making such arrangement, an angle ε2' of an off-axis principal light ray incident on the rear-side lens group GR becomes smaller than the angle of view 22. In this case, the light-beam diameter in the rear-side lens group GR becomes small. As a result, the lens group GR1 and the lens group GR2 do not make contact.

Since the lens group GR1 and the lens group GR2 do not make contact, it is not necessary to widen the distance between the lens group GR1 and the lens group GR2 and not necessary to make small the lens diameter in each of the lens group GR1 and the lens group GR2. Consequently, it is possible to achieve both of securing a wide angle of view and size reduction of the optical system. Moreover, since it is possible to make appropriate the distance between the lens group GR1 and the lens group GR2, it is possible to secure an appropriate stereoscopic effect.

A distance A and a distance L in FIG. 1B, paraxially, are defined by the following expression.

$$A = -L \times f1/f2$$

where,

A denotes a predetermined distance,

L denotes a distance between an optical axis AX1 of the lens group GR1 and an optical axis AX2 of the lens group GR2, f1 denotes a focal length of the first lens group G1, f2 denotes a focal length of the second lens group G2, and the predetermined distance is a distance between the lens group GR1 and the lens group GR2, on the object side of the first lens group G1.

The distance L is a distance between the optical axis AX1 of the lens group GR1 and the optical axis AX2 of the lens group GR2, in the rear-side lens group GR. The distance L is converted by the first lens group G1 and the second lens group G2. As a result, on the object side of the first lens group, the distance between the optical axis AX1 of the lens group GR1 and the optical axis AX2 of the lens group GR2 becomes A.

The aperture stop S is disposed in each of the lens group GR1 and the lens group GR2. When the aperture stop AS is deemed as an object, an image of the aperture stop S is formed by the first lens group G1 and the second lens group G2. The image of the aperture stop S is called as an entrance pupil. In FIG. 1B, the entrance pupil is denoted by ENP.

It is possible to approximate a value of a distance between a center of one entrance pupil and a center of the other entrance pupil (hereinafter, referred to as the 'central distance of entrance pupil') by a value of the distance A. The central distance of entrance pupil corresponds to a distance between human eyes. A value of a central distance is a value that determines the stereoscopic effect.

In the stereoscopic vision endoscope objective optical system of the present embodiment, conditional expression (1) is satisfied. Conditional expression (1) is a condition which makes small an inclination of an off-axis principal light ray incident on the rear-side lens group.

In a case in which a value falls below a lower limit value of conditional expression (1), the refractive power of the negative lens becomes excessively large. In this case, since an aberration correction becomes difficult, a sharp optical image is not formed. In a case in which the value exceeds an upper limit value of conditional expression (1), it is not possible to make the inclination of the off-axis principal light ray adequately small. Consequently, the optical system becomes large or the wide angle of view cannot be secured.

It is preferable that the following conditional expression (1') be satisfied instead of conditional expression (1).

$$0.3 < -f21n/fSUB \leq 3 \qquad (1')$$

In the stereoscopic vision endoscope objective optical system of the present embodiment, it is preferable that the first sub group have a positive refractive power, and include, in order from the object side, the negative lens and a positive lens, and the following conditional expression (2) be satisfied:

$$0.2 \text{ mm} \leq -L \times f1/f2 \leq 2 \text{ mm} \qquad (2)$$

where,

L denotes a distance between the optical axis of the first rear group and the optical axis of the second rear group, f1 denotes a focal length of the first lens group, and f2 denotes a focal length of the second lens group.

Conditional expression (2) is a conditional expression related to the distance A. As aforementioned, since the distance A corresponds to the central distance, conditional expression (2) corresponds to a conditional expression related to the central distance of the entrance pupils. Therefore, by satisfying conditional expression (2), it is possible to obtain an appropriate stereoscopic effect.

In a case in which a value falls below a lower limit value of conditional expression (2), the stereoscopic effect becomes excessively small. Accordingly, a practical stereoscopic viewing is not possible. In a case in which the value exceeds the upper limit value of conditional expression (2), the stereoscopic effect becomes excessively large. In this case, since fusing of images becomes difficult, a practical stereoscopic viewing is not possible.

It is more preferable to satisfy the following conditional expression (2') instead of conditional expression (2).

$$0.35 \text{ mm} \leq -L \times f1/f2 \leq 2 \text{ mm} \qquad (2')$$

In the stereoscopic vision endoscope objective optical system of the present embodiment, it is preferable that the second sub group include a front-side sub group having a negative refractive power and a rear-side sub group having a positive refractive power, and focusing be carried out by moving the front-side sub group along an optical axis.

In observation by a stereoscopic vision endoscope, first, a wide range is observed, and a lesion is found from the range. When the lesion is found, a front-end portion is moved closer to the lesion, and magnified observation of the lesion is carried out. It is desirable that an appropriate stereoscopic vision be achieved by both the observation of a wide range and the magnified observation.

For this, it is desirable to impart a focusing function to the optical system. In the stereoscopic vision endoscope objective optical system of the present embodiment, the front-side sub group moves along the optical axis. It is possible to make a focal length of the front-side sub group shorter than the focal length of the first lens group and the focal length of the second lens group. Consequently, it is possible to make small an amount of movement at the time of focusing.

When it is possible to make small the amount of movement at the time of focusing, it possible to reduce a size of a moving mechanism. Moreover, since it is possible to narrow a distance between adjacent lenses, it is possible to lower a light-ray height in the front-side sub group. Accordingly, it is possible to realize an optical system having a small-size and a focusing function.

Moreover, the front-side sub group is disposed in both of the first rear group and the second rear group. In this case, since it is possible to move the two front-side sub groups integrally, it is possible to make small a volume in a range of movement. As a result, it is possible to reduce a size of the moving mechanism.

Moreover, since the lens having a negative refractive power is moved, it is possible to make large an observation magnification at the time of magnified observation. As a result, it is possible to achieve even larger magnification effect.

In the stereoscopic vision endoscope objective optical system of the present embodiment, it is preferable that a positive lens be located nearest to the object in the rear-side sub group, and the following conditional expression (3) be satisfied:

$$0.6 \leq f22R1/f22R \leq 1.9 \qquad (3)$$

where, f22R1 denotes a focal length of the positive lens, and f22R denotes a focal length of the rear-side sub group.

The front-side sub group is disposed on the object side of the rear-side sub group. The refractive power of the front-side sub group being a negative refractive power, a light beam emerged from the front-side sub group is susceptible to diverge. By disposing the positive lens nearest to the object in the rear-side sub group, it is possible to suppress divergence of the light beam emerged from the front-side sub group.

In a case in which a value exceeds an upper limit value of conditional expression (3), it becomes difficult to suppress the divergence of the light beam emerged from the front-side sub group. In this case, a lens diameter in the rear-side sub group becomes larger. In the rear-side lens group, two rear-side sub groups are disposed in parallel. The lens diameter becomes large in each of the two rear-side sub groups. Consequently, the two rear-side sub groups make contact.

In order that the two rear-side sub groups do not make contact, either a distance between the two rear-side sub groups is to be widened or the lens diameter is to be made small in each of the two rear-side sub groups.

However, when the distance between the two rear-side sub groups is widened, the optical system becomes large. When the lens diameter is made small in each of the two rear-side sub groups, an effective aperture becomes small. Consequently, the angle of view becomes narrow.

In a case in which a value falls below a lower limit value of conditional expression (3), an off-axis principal light ray is refracted largely. Consequently, a coma increases. As a result, an imaging performance in a peripheral portion of an optical image is degraded.

In the stereoscopic vision endoscope objective optical system of the present embodiment, it is preferable that the first sub group include, in order from the object side, the negative lens and a positive lens, the rear-side sub group in the second sub group include, in order from the object side, a positive lens, a negative lens, and a positive lens, and the following conditional expression (4) be satisfied:

$$0.9 \leq -f21n/f21p \leq 1.5 \quad (4)$$

where, f21n denotes the focal length of the negative lens in the first sub group, and f21p denotes a focal length of the positive lens in the first sub group.

By the rear-side sub group including the positive lens, negative lens, and the positive lens, it is possible to make large the refractive power of each lens. Consequently, it is possible to assemble the rear-side sub group easily.

In a case in which a value falls below a lower limit value of conditional expression (4), it becomes difficult to correct a curvature of field which occurs in the negative lens of the first sub group and the positive lens of the first sub group. In a case in which the value exceeds the upper limit value of conditional expression (4), an effect of making a light ray refract in the first sub group becomes small. In this case, an outer diameter of a lens located nearest to the object in the first lens group becomes large. Consequently, it becomes difficult to reduce the size of the optical system.

In the stereoscopic vision endoscope objective optical system of the present embodiment, it is preferable that the first sub group include, in order from the object side, the negative lens and a positive lens, and the rear-side sub group in the second sub group include, in order from the object side, a positive lens, a positive lens, and a negative lens, and the following conditional expression (4') is satisfied:

$$0.5 \leq -f21n/f21p \leq 1 \quad (4')$$

where, f21n denotes the focal length of the negative lens in the first sub group, and f21p denotes a focal length of the positive lens in the first sub group.

By the rear-side sub group including the positive lens, the positive lens, and the negative lens, an aberration correction in the rear-side sub group becomes easy. As a result, it is possible to form an optical image with a high resolution.

In a case in which a value falls below a lower limit value of conditional expression (4'), an off-axis principal light ray is refracted largely in the first sub group. Consequently, correction of an off-axis aberration becomes difficult. In a case in which the value exceeds a lower limit value of conditional expression (4'), the refractive power of the negative lens in the first sub group becomes small or the refractive power of the positive lens in the first sub group becomes large. Consequently, correction of a spherical aberration becomes difficult.

An endoscope according to the present embodiment is characterized by including the stereoscopic vision endoscope objective optical system according to the present embodiment, and an image sensor which captures an optical image formed by the stereoscopic vision endoscope objective optical system.

According to the endoscope of the present embodiment, it is possible to observe a sharp stereoscopic image with an appropriate stereoscopic effect at the time of near-point observation.

Examples of the stereoscopic vision optical system will be described below in detail by referring to the accompanying diagrams. However, the present disclosure is not restricted to the examples described below.

Figure 2:
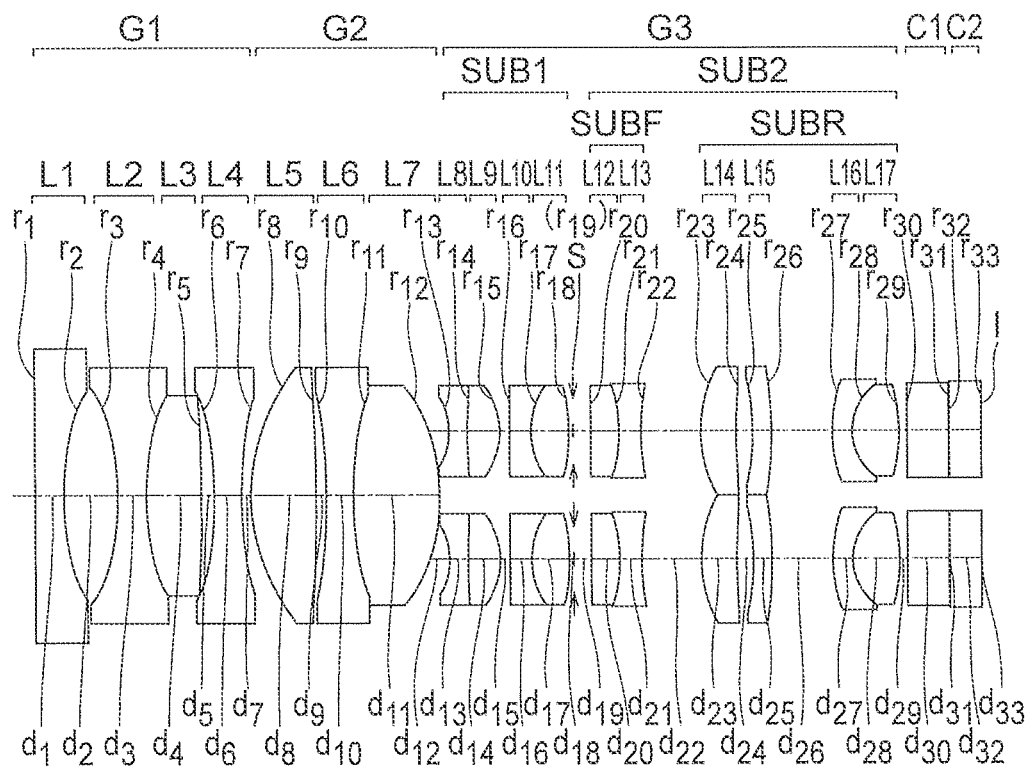
FIG. 2 is a lens cross-sectional view of a stereoscopic vision endoscope objective optical system of an example 1.

Lens cross-sectional views of each example will be described below. FIG. 2 is a lens cross-sectional view of an optical system when an object position which corresponds to a most focused image plane is fixed. Moreover, lens cross-sectional views other than FIG. 2 are lens cross-sectional views of optical systems in which the object position to be focused is variable.

In these lens cross-sectional views, FIG. 4A, FIG. 6A, FIG. 8A, and FIG. 10A are lens cross-sectional views at the time of focusing to a far point (at the time of far-point observation). FIG. 4B, FIG. 6B, FIG. 8B, and FIG. 10B are lens cross-sectional views at the time of focusing to a near point (at the time of near-point observation).

A first lens group is denotes by G1, a second lens group is denoted by G2, a third lens group is denotes by G3, an aperture stop is denoted by S, and an image plane (image pickup surface) is denoted by I. Moreover, a cover glass C1 and a cover glass C2 are disposed between the third lens group G3 and the image plane I.

The third lens group G3 is the rear-side lens group. The third lens group G3 includes the first rear group and the second rear group. An optical system same as the first rear group is used for the second rear group.

Figure 3A:
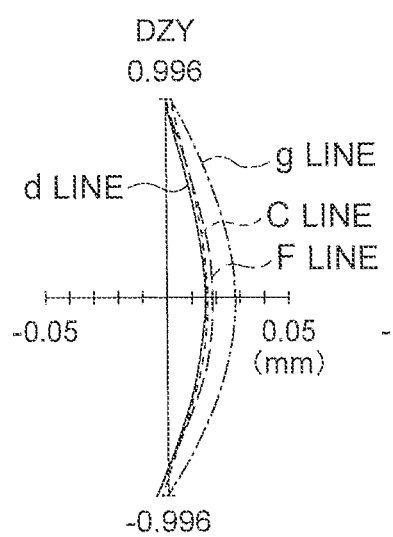
FIG. 3A, FIG. 3B, and FIG. 3C are aberration diagrams of the stereoscopic vision endoscope objective optical system of the example 1.
Figure 3B:
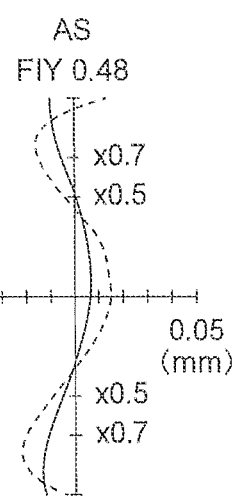
Figure 3C:
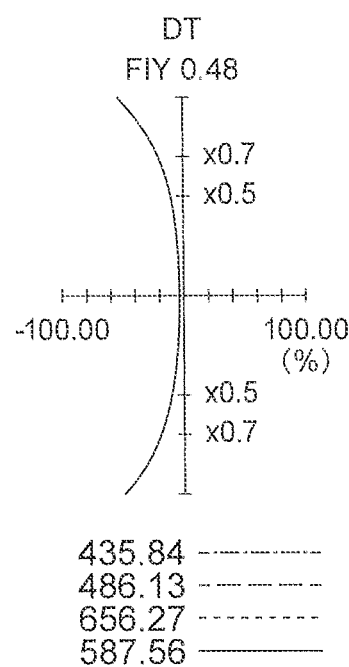
Figure 4A:
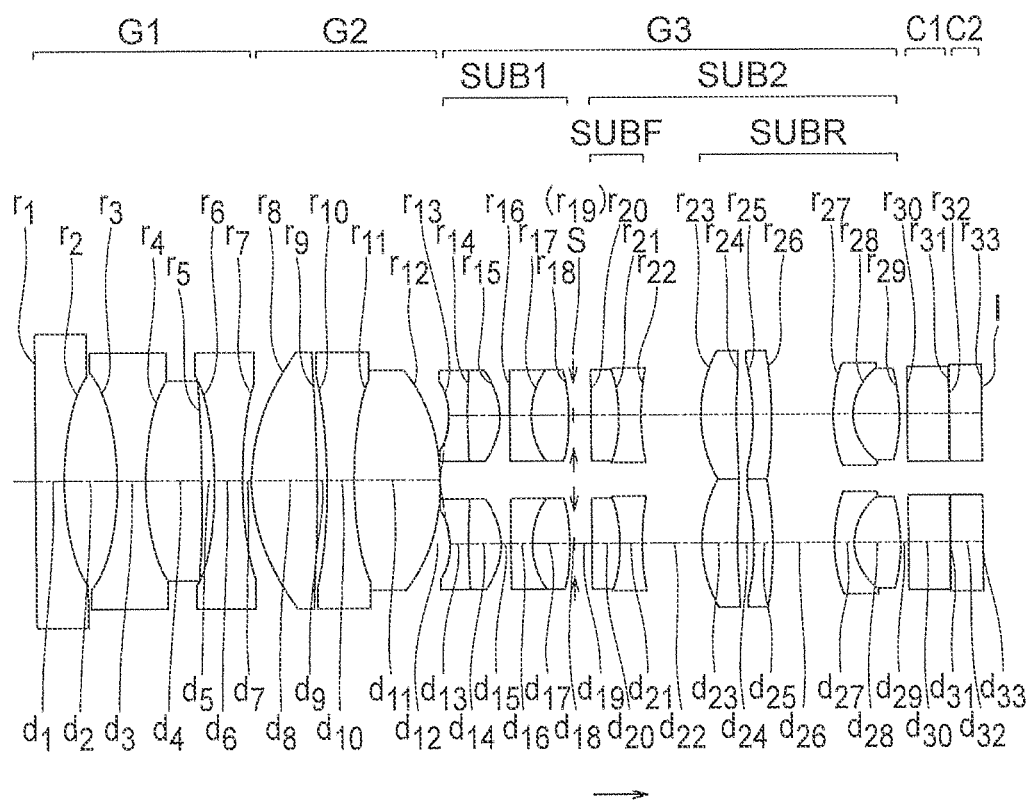
FIG. 4A and FIG. 4B are lens cross-sectional views of a stereoscopic vision endoscope objective optical system of an example 2.
Figure 4B:
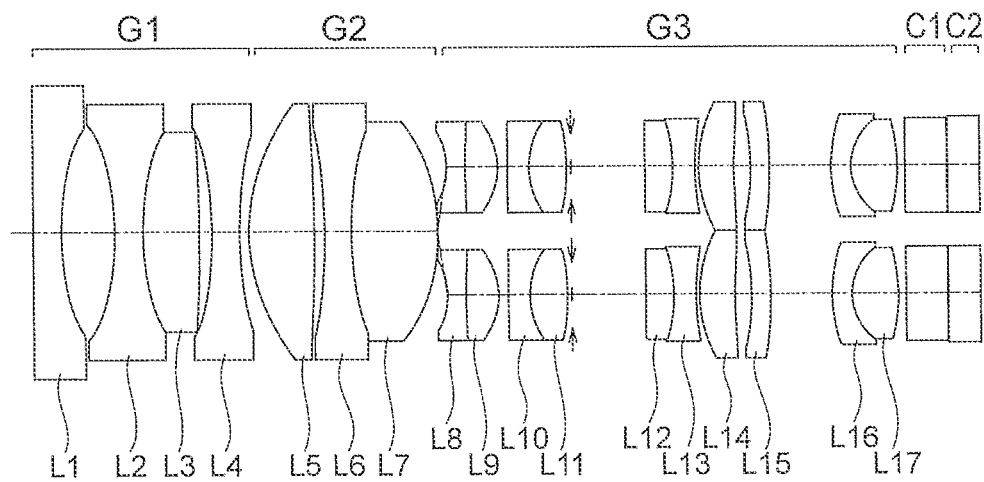
Figure 5A:
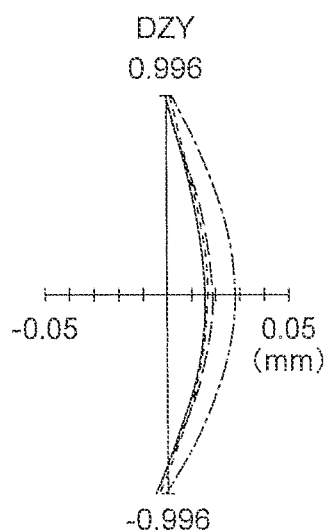
FIG. 5A, FIG. 5B, FIG. 5C, FIG. 5D, FIG. 5E, and FIG. 5F are aberration diagrams of the stereoscopic vision endoscope objective optical system of the example 2.
Figure 5B:
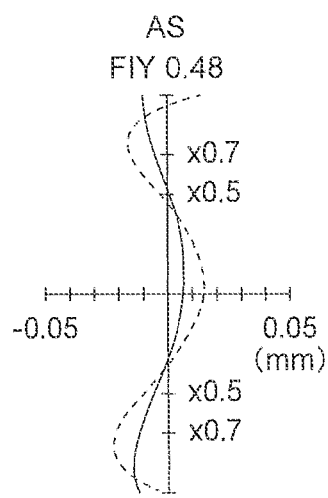
Figure 5C:
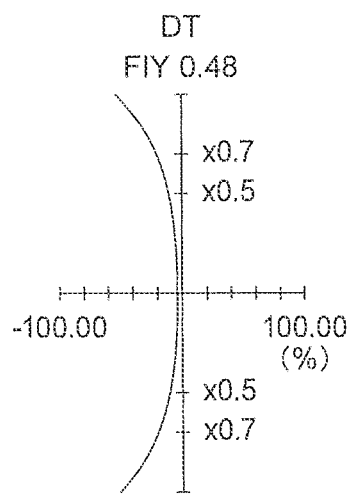
Figure 5D:
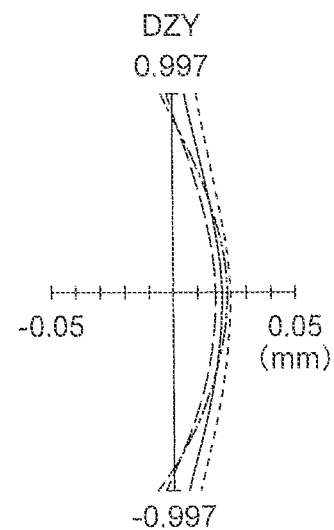
Figure 5E:
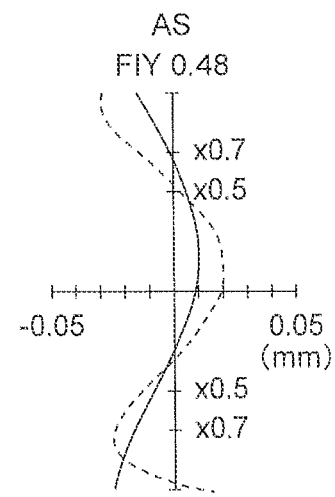
Figure 5F:
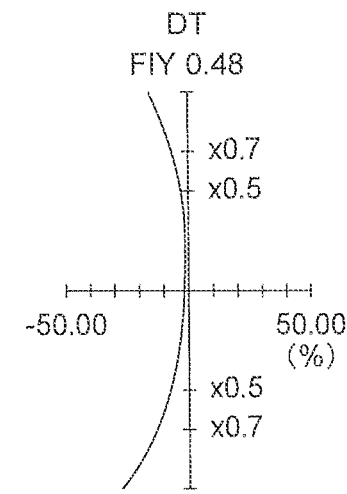
Figure 6A:
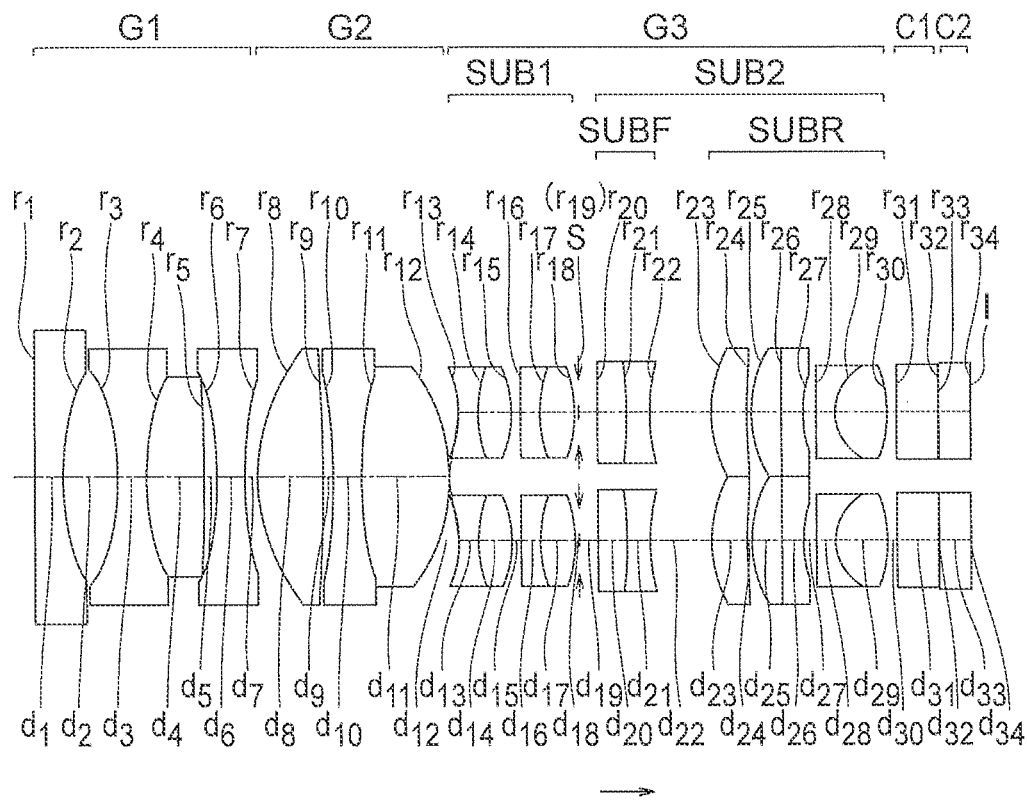
FIG. 6A and FIG. 6B are lens cross-sectional views of a stereoscopic vision endoscope objective optical system of an example 3.
Figure 6B:
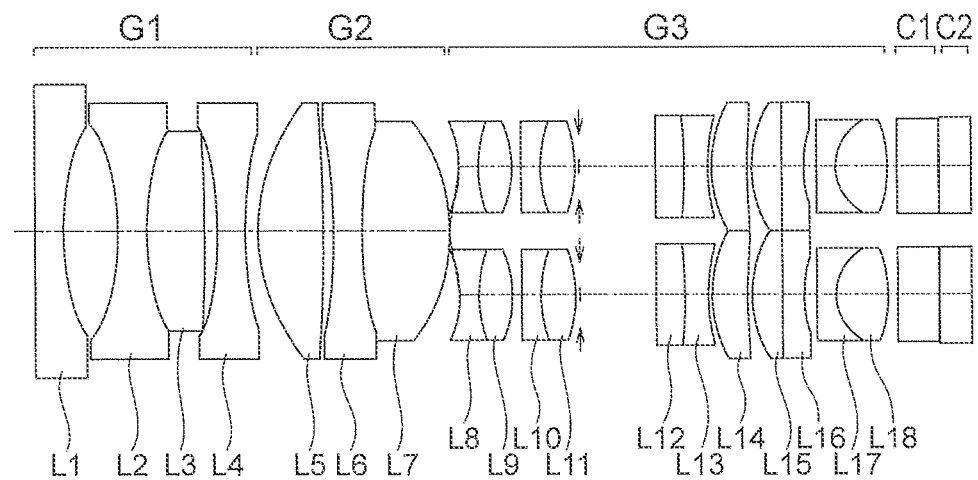
Figure 7A:
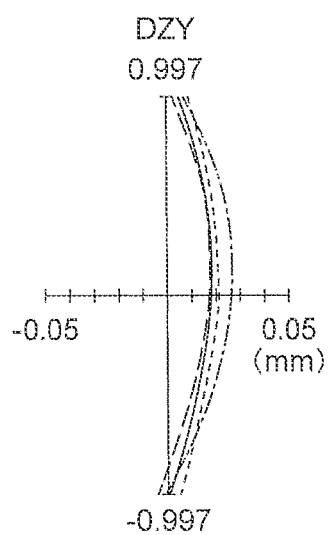
FIG. 7A, FIG. 7B, FIG. 7C, FIG. 7D, FIG. 7E, and FIG. 7F are aberration diagrams of the stereoscopic vision endoscope objective optical system of the example 3.
Figure 7B:
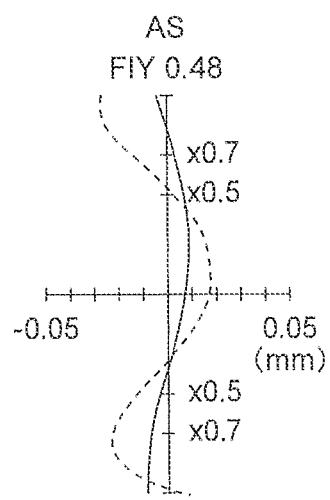
Figure 7C:
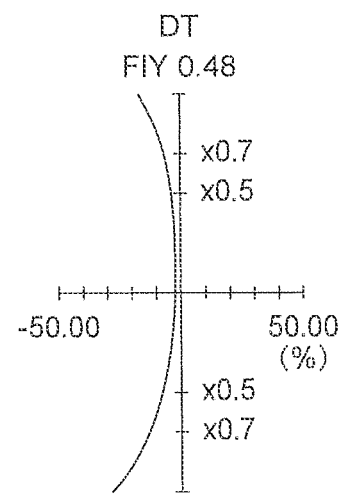
Figure 7D:
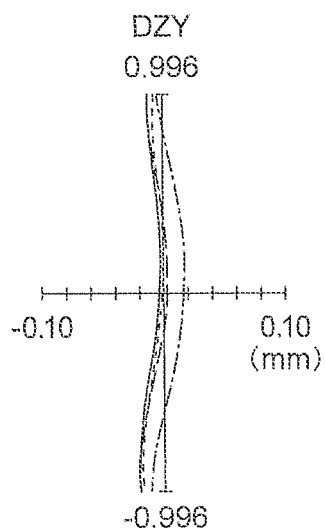
Figure 7E:
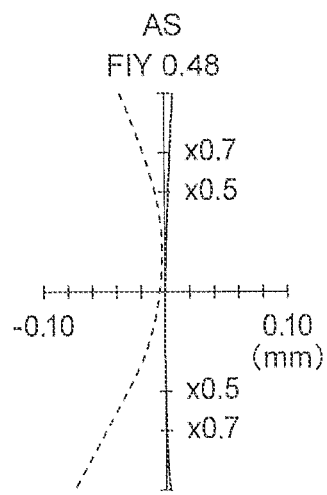
Figure 7F:
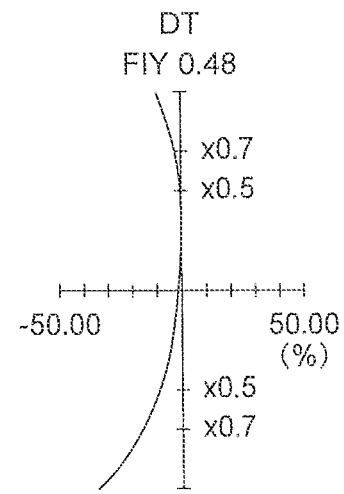
Figure 8A:
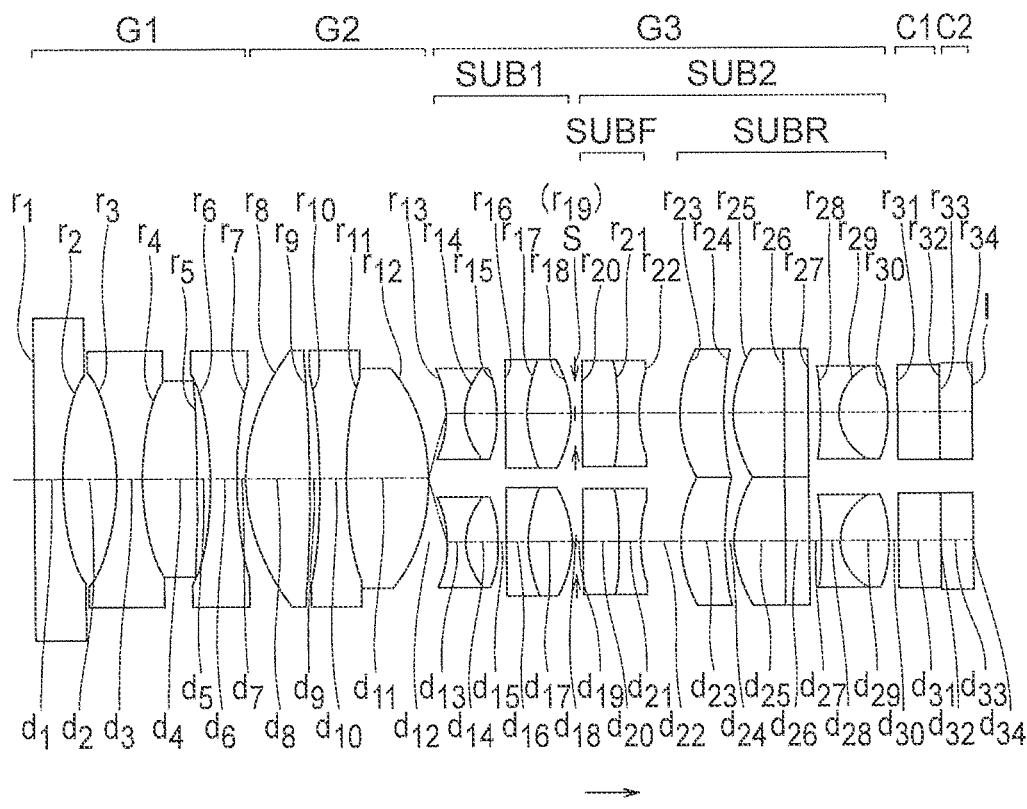
FIG. 8A and FIG. 8B are lens cross-sectional views of a stereoscopic vision endoscope objective optical system of an example 4.
Figure 8B:
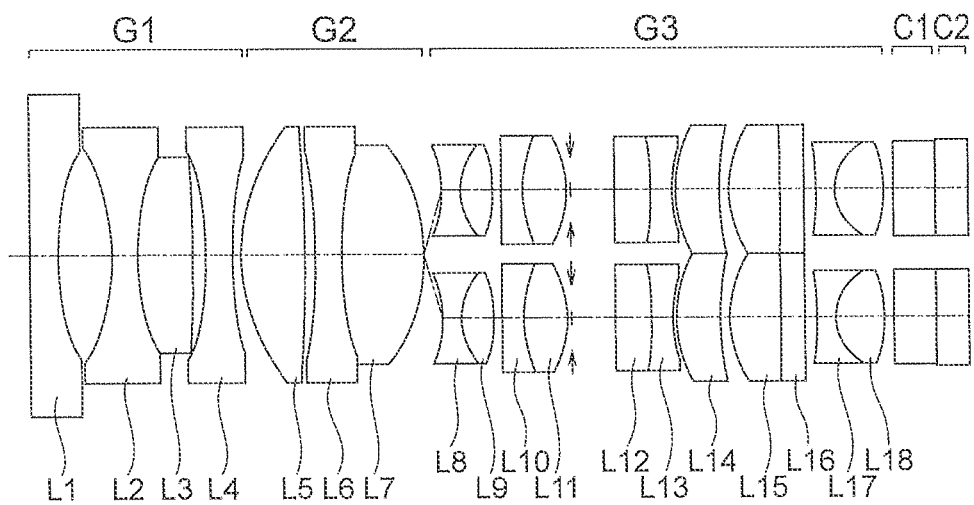
Figure 9A:
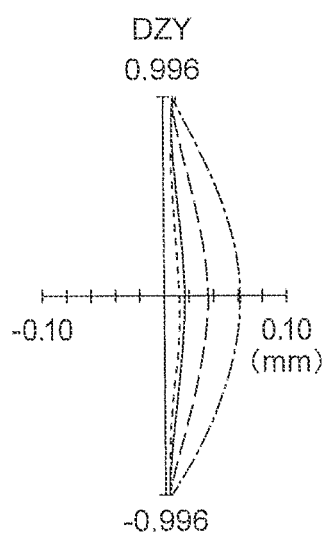
FIG. 9A, FIG. 9B, FIG. 9C, FIG. 9D, FIG. 9E, and FIG. 9F are aberration diagrams of the stereoscopic vision endoscope objective optical system of the example 4.
Figure 9B:
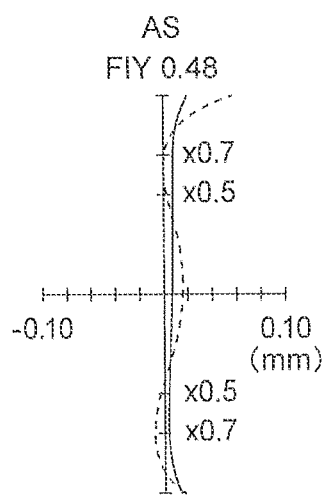
Figure 9C:
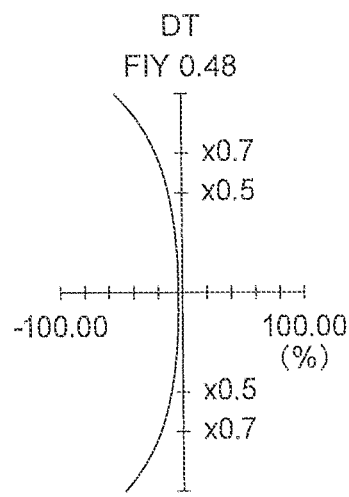
Figure 9D:
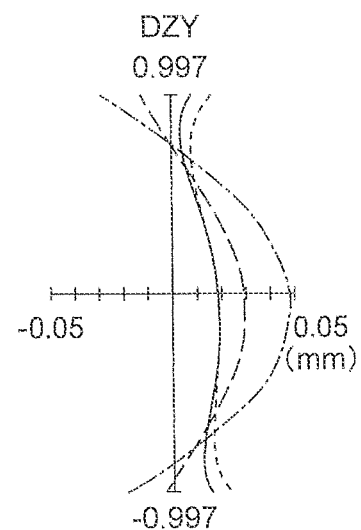
Figure 9E:
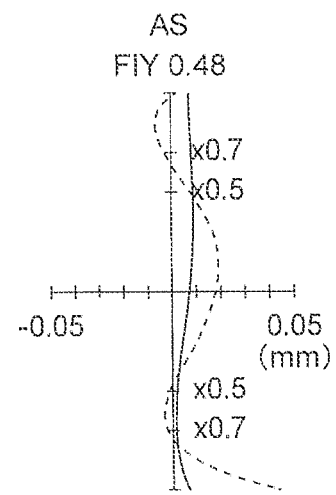
Figure 9F:
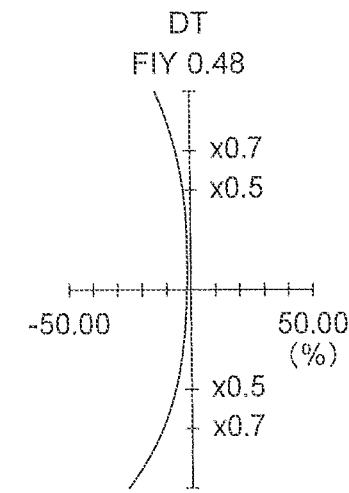
Figure 10A:
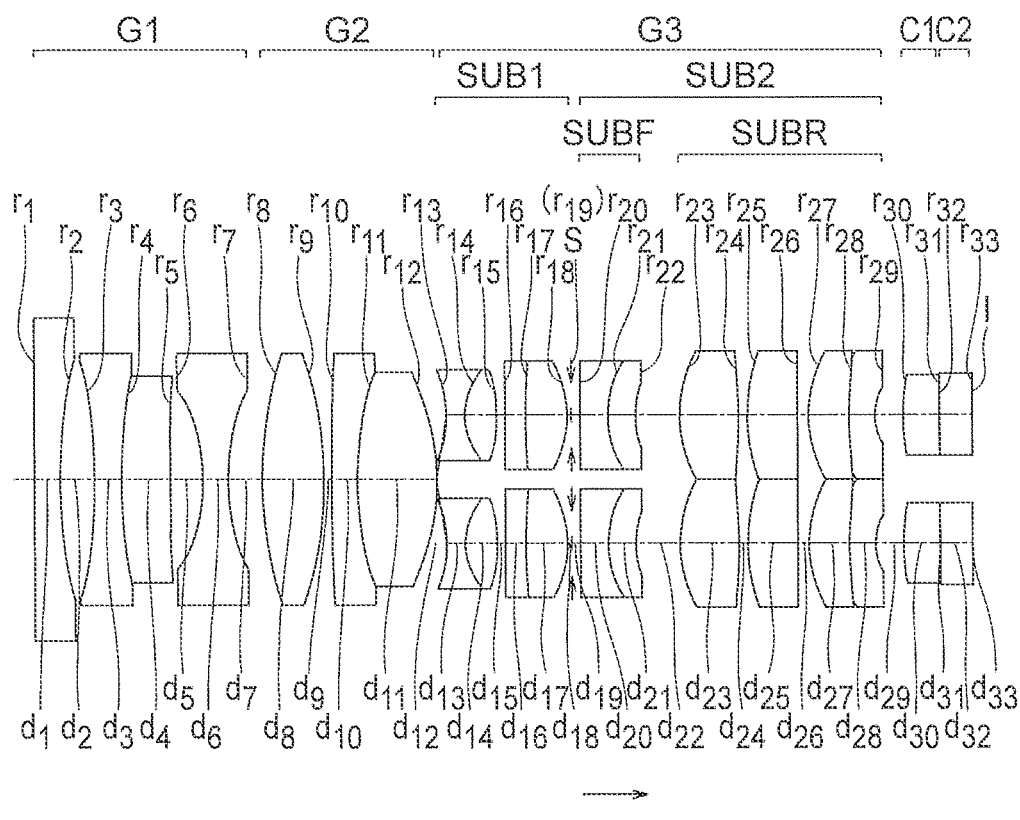
FIG. 10A and FIG. 10B are lens cross-sectional views of a stereoscopic vision endoscope objective optical system of an example 5.
Figure 10B:
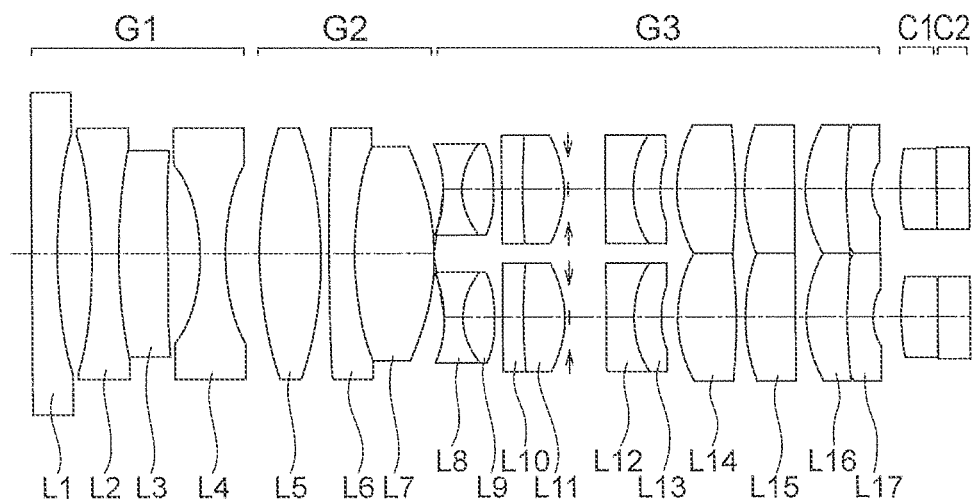
Figure 11A:
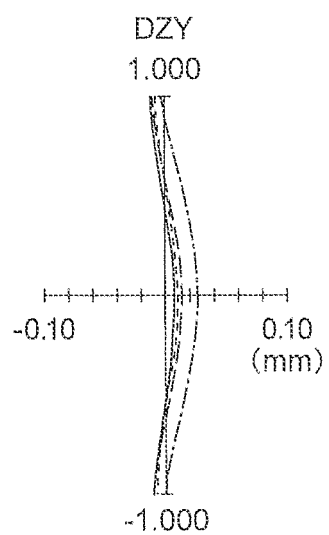
FIG. 11A, FIG. 11B, FIG. 11C, FIG. 11D, FIG. 11E, and FIG. 11F are aberration diagrams of the stereoscopic vision endoscope objective optical system of the example 5.
Figure 11B:
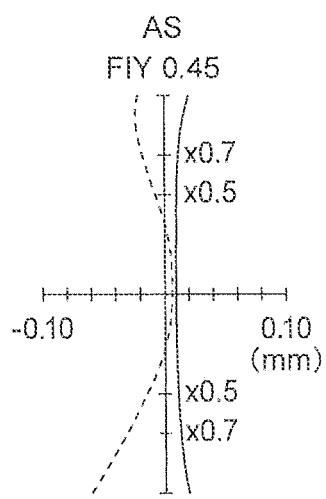
Figure 11C:
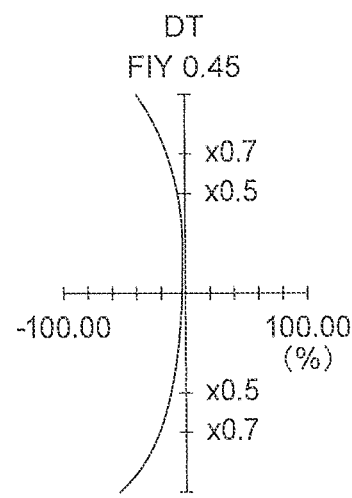
Figure 11D:
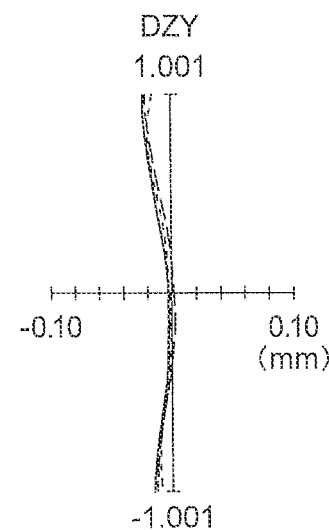
Figure 11E:
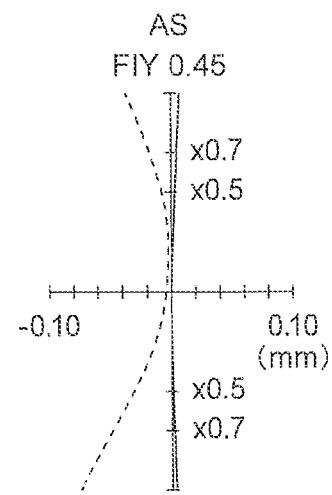
Figure 11F:
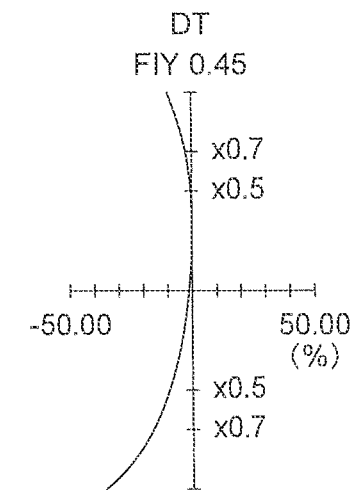

Aberration diagrams of each example will be described below. FIG. 3A shows a transverse aberration (DZY), FIG. 3B shows an astigmatism (AS), and FIG. 3C shows a distortion (DT). Each aberration diagram is an aberration diagram for the object position which corresponds to the most focused image plane.

FIG. 5A, FIG. 7A, FIG. 9A, and FIG. 11A show a transverse aberration (DZY) at the time of focusing to the far point.

FIG. 5B, FIG. 7B, FIG. 9B, and FIG. 11B show an astigmatism (AS) at the time of focusing to the far point.

FIG. 5C, FIG. 7C, FIG. 9C, and FIG. 11C show a distortion (DT) at the time of focusing to the far point.

FIG. 5D, FIG. 7D, FIG. 9D, and FIG. 11D show a transverse aberration (DZY) at the time of focusing to the near point.

FIG. 5E, FIG. 7E, FIG. 9E, and FIG. 11E show an astigmatism (AS) at the time of focusing to the near point.

FIG. 5F, FIG. 7F, FIG. 9F, and FIG. 11F show a distortion (DT) at the time of focusing to the near point.

In each aberration diagram, a horizontal axis indicates an aberration amount. The unit of aberration amount for the transverse aberration and the astigmatism is mm. Moreover, the unit of aberration amount for the distortion is %. The unit of a wavelength of an aberration curve is nm.

A stereoscopic vision endoscope objective optical system of an example 1 includes, in order from an object side, a first lens group G1 having a negative refractive power, a second lens group G2 having a positive refractive power, and a third lens group G3 having a positive refractive power.

The first lens group G1 includes a planoconcave negative lens L1 having a flat surface directed toward the object side, a biconcave negative lens L2, a biconvex positive lens L3, and a biconcave negative lens L4. Here, a cemented lens is formed by the biconcave negative lens L2 and the biconvex positive lens L3.

The second lens group G2 includes a biconvex positive lens L5, a biconcave negative lens L6, and a biconvex positive lens L7. Here, a cemented lens is formed by the biconcave negative lens L6 and the biconvex positive lens L7.

The third lens group G3 includes a first rear group and a second rear group. Both the first rear group and the second rear group include a biconcave negative lens L8, a biconvex positive lens L9, a planoconcave negative lens L10 having a flat surface directed toward the object side, a biconvex positive lens L11, a planoconvex positive lens L12 having a flat surface directed toward the object side, a biconcave negative lens L13, a positive meniscus lens L14 having a convex surface directed toward the object side, a negative meniscus lens L15 having a convex surface directed toward an image side, a negative meniscus lens L16 having a convex surface directed toward the object side, and a biconvex positive lens L17.

Here, a first cemented lens is formed by the biconcave negative lens L8 and the biconvex positive lens L9. A second cemented lens is formed by the planoconcave negative lens L10 and the biconvex positive lens L11. A third cemented lens is formed by the planoconvex positive lens L12 and the biconcave negative lens L13. A fourth cemented lens is formed by the negative meniscus lens L16 and the biconvex positive lens L17.

Both the first rear group and the second rear group consist of a first sub group SUB1 having a positive refractive power and a second sub group SUB2. An aperture stop (a stop) S is disposed between the first sub group SUB1 and the second sub group SUB2.

The first sub group SUB1 consists of the first cemented lens and the second cemented lens. The second sub group SUB2 consists of a front-side sub group SUBF having a negative refractive power and a rear-side sub group SUBR having a positive refractive power. The front-side sub group SUBF consists of the third cemented lens. The rear-side sub group SUBR consists of a positive lens, a negative lens, and the fourth cemented lens.

The stereoscopic vision endoscope objective optical system of the example 1 is not provided with a focusing function.

An aspheric surface is provided to a total of two surfaces, which are an object-side surface of the biconcave negative lens L4 and an object-side surface of the biconcave negative lens L6.

A stereoscopic vision endoscope objective optical system of an example 2 includes, in order from an object side, a first lens group G1 having a negative refractive power, a second lens group G2 having a positive refractive power, and a third lens group G3 having a positive refractive power.

The first lens group G1 includes a planoconcave negative lens L1 having a flat surface directed toward the object side, a biconcave negative lens L2, a biconvex positive lens L3, and a biconcave negative lens L4. Here, a cemented lens is formed by the biconcave negative lens L2 and the biconvex positive lens L3.

The second lens group G2 includes a biconvex positive lens L5, a biconcave negative lens L6, and a biconvex positive lens L7. Here, a cemented lens is formed by the biconcave negative lens L6 and the biconvex positive lens L7.

The third lens group G3 includes a first rear group and a second rear group. Both the first rear group and the second rear group include a biconcave negative lens L8, a biconvex positive lens L9, a planoconcave negative lens L10 having a flat surface directed toward the object side, a biconvex positive lens L11, a planoconvex positive lens L12 having a flat surface directed toward the object side, a biconcave negative lens L13, a positive meniscus lens L14 having a convex surface directed toward the object side, a negative meniscus lens L15 having a convex surface directed toward an image side, a negative meniscus lens L16 having a convex surface directed toward the object side, and a biconvex positive lens L17.

Here, a first cemented lens is formed by the biconcave negative lens L8 and the biconvex positive lens L9. A second cemented lens is formed by the planoconcave negative lens L10 and the biconvex positive lens L11. A third cemented lens is formed by the planoconvex positive lens L12 and the biconcave negative lens L13. A fourth cemented lens is formed by the negative meniscus lens L16 and the biconvex positive lens L17.

Both the first rear group and the second rear group consist of a first sub group SUB1 having a positive refractive power and a second sub group SUB2. An aperture stop (a stop) S is disposed between the first sub group SUB1 and the second sub group SUB2.

The first sub group SUB1 consists of the first cemented lens and the second cemented lens. The second sub group SUB2 consists of a front-side sub group SUBF having a negative refractive power and a rear-side sub group SUBR having a positive refractive power. The front-side sub group SUBF consists of the third cemented lens. The rear-side sub group SUBR consists of a positive lens, a negative lens, and the fourth cemented lens.

The stereoscopic vision endoscope objective optical system of the example 2 is provided with a focusing function. At the time of focusing from a far point to a near point, the front-side sub group SUBF moves toward the image side. In the stereoscopic vision objective optical system of the example 2, since the front-side sub group SUBF in the first rear group and the front-side sub group SUBF in the second rear group are to be moved simultaneously, it is possible to simplify a moving mechanism.

An aspheric surface is provided to a total of two surfaces, which are an object-side surface of the biconcave negative lens L4 and an object-side surface of the biconcave negative lens L6.

A stereoscopic vision endoscope objective optical system of an example 3 includes, in order from an object side, a first lens group G1 having a negative refractive power, a second lens group G2 having a positive refractive power, and a third lens group G3 having a positive refractive power.

The first lens group G1 includes a planoconcave negative lens L1 having a flat surface directed toward the object side, a biconcave negative lens L2, a biconvex positive lens L3, and a biconcave negative lens L4. Here, a cemented lens is formed by the biconcave negative lens L2 and the biconvex positive lens L3.

The second lens group G2 includes a biconvex positive lens L5, a biconcave negative lens L6, and a biconvex positive lens L7. Here, a cemented lens is formed by the biconcave negative lens L6 and the biconvex positive lens L7.

The third lens group G3 includes a first rear group and a second rear group. Both the first rear group and the second rear group include a biconcave negative lens L8, a biconvex positive lens L9, a planoconcave negative lens L10 having a flat surface directed toward the object side, a biconvex positive lens L11, a planoconvex positive lens L12 having a flat surface directed toward the object side, a biconcave negative lens L13, a positive meniscus lens L14 having a convex surface directed toward the object side, a planoconvex positive lens L15 having a flat surface directed toward an image side, a planoconcave negative lens L16 having a flat surface directed toward the object side, a biconcave negative lens L17, and a biconvex positive lens L18.

Here, a first cemented lens is formed by the biconcave negative lens L8 and the biconvex positive lens L9. A second cemented lens is formed by the planoconcave negative lens L10 and the biconvex positive lens L11. A third cemented lens is formed by the planoconvex positive lens L12 and the biconcave negative lens L13. A fourth cemented lens is formed by the planoconvex positive lens L15 and the planoconcave negative lens L16. A fifth cemented lens is formed by the biconcave negative lens L17 and the biconvex positive lens L18.

Both the first rear group and the second rear group consist of a first sub group SUB1 having a positive refractive power and a second sub group SUB2. An aperture stop (a stop) S is disposed between the first sub group SUB1 and the second sub group SUB2.

The first sub group SUB1 consists of the first cemented lens and the second cemented lens. The second sub group SUB2 consists of a front-side sub group SUBF having a negative refractive power and a rear-side sub group SUBR having a positive refractive power. The front-side sub group SUBF consists of the third cemented lens. The rear-side sub group SUBR consists of a positive lens, the fourth cemented lens, and the fifth cemented lens.

The stereoscopic vision endoscope objective optical system of the example 3 is provided with a focusing function. At the time of focusing from a far point to a near point, the front-side sub group SUBF moves toward the image side. In the stereoscopic vision objective optical system of the example 3, since the front-side sub group SUBF in the first rear group and the front-side sub group SUBF in the second rear group are to be moved simultaneously, it is possible to simplify a moving mechanism.

An aspheric surface is provided to a total of two surfaces, which are an object-side surface of the biconcave negative lens L4 and an object-side surface of the biconcave negative lens L6.

A stereoscopic vision endoscope objective optical system of an example 4 includes, in order from an object side, a first lens group G1 having a negative refractive power, a second lens group G2 having a positive refractive power, and a third lens group G3 having a positive refractive power.

The first lens group G1 includes a planoconcave negative lens L1 having a flat surface directed toward the object side, a biconcave negative lens L2, a biconvex positive lens L3, and a biconcave negative lens L4. Here, a cemented lens is formed by the biconcave negative lens L2 and the biconvex positive lens L3.

The second lens group G2 includes a biconvex positive lens L5, a biconcave negative lens L6, and a biconvex positive lens L7. Here, a cemented lens is formed by the biconcave negative lens L6 and the biconvex positive lens L7.

The third lens group G3 includes a first rear group and a second rear group. Both the first rear group and the second rear group include a biconcave negative lens L8, a biconvex positive lens L9, a planoconcave negative lens L10 having a flat surface directed toward the object side, a biconvex positive lens L11, a planoconvex positive lens L12 having a flat surface directed toward the object side, a biconcave negative lens L13, a positive meniscus lens L14 having a convex surface directed toward the object side, a biconvex positive lens L15, a biconcave negative lens L16, a biconcave negative lens L17, and a biconvex positive lens L18.

Here, a first cemented lens is formed by the biconcave negative lens L8 and the biconvex positive lens L9. A second cemented lens is formed by the planoconcave negative lens L10 and the biconvex positive lens L11. A third cemented lens is formed by the planoconvex positive lens L12 and the biconcave negative lens L13. A fourth cemented lens is formed by the biconvex positive lens L15 and the biconcave negative lens L16. A fifth cemented lens is formed by the biconcave negative lens L17 and the biconvex positive lens L18.

Both the first rear group and the second rear group consist of a first sub group SUB1 having a positive refractive power and a second sub group SUB2. An aperture stop (a stop) S is disposed between the first sub group SUB1 and the second sub group SUB2.

The first sub group SUB1 consists of the first cemented lens and the second cemented lens. The second sub group SUB2 consists of a front-side sub group SUBF having a negative refractive power and a rear-side sub group SUBR having a positive refractive power. The front-side sub group SUBF consists of the third cemented lens. The rear-side sub group SUBR consists of a positive lens, the fourth cemented lens, and the fifth cemented lens.

The stereoscopic vision endoscope objective optical system of the example 4 is provided with a focusing function. At the time of focusing from a far point to a near point, the front-side sub group SUBF moves toward an image side. In the stereoscopic vision objective optical system of the example 4, since the front-side sub group SUBF in the first rear group and the front-side sub group SUBF in the second rear group are to be moved simultaneously, it is possible to simplify a moving mechanism.

An aspheric surface is provided to a total of two surfaces, which are an object-side surface of the biconcave negative lens L4 and an object-side surface of the biconcave negative lens L6.

A stereoscopic vision endoscope objective optical system of an example 5 includes, in order from an object side, a first lens group G1 having a negative refractive power, a second lens group G2 having a positive refractive power, and a third lens group G3 having a positive refractive power.

The first lens group G1 includes a planoconcave negative lens L1 having a flat surface directed toward the object side, a biconcave negative lens L2, a biconvex positive lens L3, and a biconcave negative lens L4. Here, a cemented lens is formed by the biconcave negative lens L2 and the biconvex positive lens L3.

The second lens group G2 includes a biconvex positive lens L5, a negative meniscus lens L6 having a convex surface directed toward the object side, and a biconvex positive lens L7. Here, a cemented lens is formed by the negative meniscus lens L6 and the biconvex positive lens L7.

The third lens group G3 includes a first rear group and a second rear group. Both the first rear group and the second rear group include a biconcave negative lens L8, a biconvex positive lens L9, a planoconcave negative lens L10 having a flat surface directed toward the object side, a biconvex positive lens L11, a planoconcave negative lens L12 having a flat surface directed toward the object side, a positive meniscus lens L13 having a convex surface directed toward the object side, a biconvex positive lens L14, a planoconvex positive lens L15 having a flat surface directed toward an image side, a positive meniscus lens L16 having a convex surface directed toward the object side, and a negative meniscus lens L17 having a convex surface directed toward the object side.

Here, a first cemented lens is formed by the biconcave negative lens L8 and the biconvex positive lens L9. A second cemented lens is formed by the planoconcave negative lens L10 and the biconvex positive lens L11. A third cemented lens is formed by the planoconcave negative lens L12 and the positive meniscus lens L13. A fourth cemented lens is formed by the positive meniscus lens L16 and the negative meniscus lens L17.

Both the first rear group and the second rear group consist of a first sub group SUB1 having a positive refractive power and a second sub group SUB2. An aperture stop (a stop) S is disposed between the first sub group SUB1 and the second sub group SUB2.

The first sub group SUB1 consists of the first cemented lens and the second cemented lens. The second sub group SUB2 consists of a front-side sub group SUBF having a negative refractive power and a rear-side sub group SUBR having a positive refractive power. The front-side sub group SUBF consists of the third cemented lens. The rear-side sub group SUBR consists of a positive lens, a positive lens, and the fourth cemented lens.

The stereoscopic vision endoscope objective optical system of the example 5 is provided with a focusing function. At the time of focusing from a far point to a near point, the front-side sub group SUBF moves toward the image side. In the stereoscopic vision objective optical system of the example 5, since the front-side sub group SUBF in the first rear group and the front-side sub group SUBF in the second rear group are to be moved simultaneously, it is possible to simplify a moving mechanism.

Numerical data of each example described above is shown below. In Surface data, r denotes radius of curvature of each lens surface, d denotes a distance between respective lens surfaces, nd denotes a refractive index of each lens for a d-line, and vd denotes an Abbe number for each lens.

A shape of an aspherical surface is defined by the following expression where the direction of the optical axis is represented by z, the direction orthogonal to the optical axis is represented by y, a conical coefficient is represented by K, aspherical surface coefficients are represented by A4, A6, A8, A10, A12 . . . .

$$Z=(y^2/r)/[1+\{1-(1+k)(y/r)^2\}^{1/2}]+A4y^4+A6y^6+A8y^8+A10y^{10}+A12y^{12}+ \ldots$$

Further, in the aspherical surface coefficients, 'E-n' (where, n is an integral number) indicates '$10^{-n}$'. Moreover, these symbols are commonly used in the following numerical data for each example.

In the present example, a combined focal length is calculated in order from a lens on an object-surface side, and a lens range for which the combined focal length is the maximum (lens range for which the negative refractive power becomes maximum) is defined as the first lens group G1. However, the definition of the first lens group G1 is not restricted to the abovementioned definition.

Moreover, in various data, IH denotes an image height, ϕ denotes a diameter of the aperture stop, L denotes a distance between an optical axis of the first rear group and an optical axis of the second rear group, NA denotes a numerical aperture on the object side, and AI denotes an amount of shift of the image plane.

An amount of shift of the third lens group is to be calculated from a distance between an optical axis of the first lens group and the optical axis of the first rear group or a distance between the optical axis of the first lens group and the optical axis of the second rear group.

A first optical image is formed on an image plane of the first rear group. A second optical image is formed on an image plane of the second rear group. Both a position of the optical axis of the first rear group and a position of the optical axis of the second rear group shift with respect to the optical axis of the first lens group. Therefore, an image of an object point on the optical axis of the first lens group is not formed on the optical axis of the first rear group and the optical axis of the second rear group. In other words, a center of the first optical image does not coincide with the optical axis of the first rear group, and a center of the second optical image does not coincide with the optical axis of the second rear group.

An amount of shift of the image plane is to be calculated from a difference in the optical axis of the first rear group and the center of the first optical image or to be calculated from a difference in the optical axis of the second rear group and the center of the second optical image. The plus or minus of sign of the amount of shift of the image plane is negative in a case in which the center of the first optical image is located on an optical-axis side of the first lens group than the optical axis of the first rear group, and in a case in which the center of the second optical image is located on the optical-axis side of the first lens group than the optical axis of the second rear group.

Example 1

| Unit mm | | | | |
|---|---|---|---|---|
| Surface data | | | | |
| Surface no. | r | d | nd | vd |
| Object plane | ∞ | 10.0000 | | |
| 1 | ∞ | 0.3000 | 1.88300 | 40.76 |
| 2 | 2.7003 | 0.6100 | | |

-continued

Unit mm

| | | | | |
|---|---|---|---|---|
| 3 | −2.4659 | 0.3000 | 1.81600 | 46.62 |
| 4 | 2.7009 | 0.6100 | 1.92286 | 18.90 |
| 5 | −18.5670 | 0.1500 | | |
| 6* | −4.6983 | 0.3000 | 1.51633 | 64.14 |
| 7 | 4.6936 | 0.1025 | | |
| 8 | 2.1908 | 0.7300 | 1.69680 | 55.53 |
| 9 | −15.9753 | 0.1000 | | |
| 10* | −13.1672 | 0.3000 | 1.85026 | 32.27 |
| 11 | 4.0126 | 0.9500 | 1.49700 | 81.54 |
| 12 | −2.0357 | 0.1000 | | |
| 13 | −0.8235 | 0.2100 | 1.95906 | 17.47 |
| 14 | 8.3698 | 0.3600 | 1.48749 | 70.23 |
| 15 | −0.7912 | 0.1000 | | |
| 16 | ∞ | 0.2400 | 1.81600 | 46.62 |
| 17 | 0.8312 | 0.4200 | 1.80518 | 25.42 |
| 18 | −2.0255 | 0.0500 | | |
| 19 (Stop) | ∞ | 0.19262 | | |
| 20 | ∞ | 0.3100 | 1.80610 | 40.92 |
| 21 | −1.4007 | 0.2400 | 1.75520 | 27.51 |
| 22 | 2.6888 | 0.65738 | | |
| 23 | 1.4452 | 0.3900 | 2.00330 | 28.27 |
| 24 | 7.8217 | 0.1851 | | |
| 25 | −2.5095 | 0.2038 | 1.92286 | 18.90 |
| 26 | −3.9683 | 0.6793 | | |
| 27 | 1.6582 | 0.2100 | 1.95906 | 17.47 |
| 28 | 0.6086 | 0.5100 | 1.48749 | 70.23 |
| 29 | −1.8356 | 0.1000 | | |
| 30 | ∞ | 0.4500 | 1.51633 | 64.14 |
| 31 | ∞ | 0.0100 | 1.51300 | 64.00 |
| 32 | ∞ | 0.3500 | 1.50510 | 63.26 |
| 33 | ∞ | 0.0000 | | |
| Image plane | ∞ | | | |

Aspherical surface data

6th surface k = −1.0541
A4 = −4.4267E−02, A6 = 6.8814E−03, A8 = 3.0686E−03

10th surface k = −0.2974
A4 = −2.3416E−02, A6 = −7.5181E−03

Various data

| | |
|---|---|
| IH | 0.48 |
| φ | 0.72 |
| L | 1.4 |
| NA | 0.00795 |
| ΔI | 0.01393 |

Example 2

Unit mm

Surface data

| Surface no. | r | d | nd | vd |
|---|---|---|---|---|
| Object plane | ∞ | d0 | | |
| 1 | ∞ | 0.3000 | 1.88300 | 40.76 |
| 2 | 2.7003 | 0.6100 | | |
| 3 | −2.4659 | 0.3000 | 1.81600 | 46.62 |
| 4 | 2.7009 | 0.6100 | 1.92286 | 18.90 |
| 5 | −18.5670 | 0.1500 | | |
| 6* | −4.6983 | 0.3000 | 1.51633 | 64.14 |
| 7 | 4.6936 | 0.1025 | | |
| 8 | 2.1908 | 0.7300 | 1.69680 | 55.53 |
| 9 | −15.9753 | 0.1000 | | |
| 10* | −13.1672 | 0.3000 | 1.85026 | 32.27 |
| 11 | 4.0126 | 0.9500 | 1.49700 | 81.54 |
| 12 | −2.0357 | 0.1000 | | |

-continued

Unit mm

| | | | | |
|---|---|---|---|---|
| 13 | −0.8235 | 0.2100 | 1.95906 | 17.47 |
| 14 | 8.3698 | 0.3600 | 1.48749 | 70.23 |
| 15 | −0.7912 | 0.1000 | | |
| 16 | ∞ | 0.2400 | 1.81600 | 46.62 |
| 17 | 0.8312 | 0.4200 | 1.80518 | 25.42 |
| 18 | −2.0255 | 0.0500 | | |
| 19 (Stop) | ∞ | d1 | | |
| 20 | ∞ | 0.3100 | 1.80610 | 40.92 |
| 21 | −1.4007 | 0.2400 | 1.75520 | 27.51 |
| 22 | 2.6888 | d2 | | |
| 23 | 1.4452 | 0.3900 | 2.00330 | 28.27 |
| 24 | 7.8217 | 0.1851 | | |
| 25 | −2.5095 | 0.2038 | 1.92286 | 18.90 |
| 26 | −3.9683 | 0.6793 | | |
| 27 | 1.6582 | 0.2100 | 1.95906 | 17.47 |
| 28 | 0.6086 | 0.5100 | 1.48749 | 70.23 |
| 29 | −1.8356 | 0.1000 | | |
| 30 | ∞ | 0.4500 | 1.51633 | 64.14 |
| 31 | ∞ | 0.0100 | 1.51300 | 64.00 |
| 32 | ∞ | 0.3500 | 1.50510 | 63.26 |
| 33 | ∞ | 0.0000 | | |
| Image plane | ∞ | | | |

Aspherical surface data

6th surface k = −1.0541
A4 = −4.4267E−02, A6 = 6.8814E−03, A8 = 3.0686E−03

10th surface k = −0.2974
A4 = −2.3416E−02, A6 = −7.5181E−03

Various data

| | | |
|---|---|---|
| IH | | 0.48 |
| φ | | 0.72 |
| L | | 1.4 |

| | far-point observation | near-point observation |
|---|---|---|
| NA | 0.00795 | 0.02626 |
| ΔI | 0.01393 | 0.05381 |
| d0 | 10 | 2 |
| d1 | 0.19262 | 0.8 |
| d2 | 0.65738 | 0.05 |

Example 3

Unit mm

Surface data

| Surface no. | r | d | nd | vd |
|---|---|---|---|---|
| Object plane | ∞ | d0 | | |
| 1 | ∞ | 0.3000 | 1.88300 | 40.76 |
| 2 | 2.7003 | 0.6100 | | |
| 3 | −2.4659 | 0.3000 | 1.81600 | 46.62 |
| 4 | 2.7009 | 0.6100 | 1.92286 | 18.90 |
| 5 | −18.5670 | 0.1500 | | |
| 6* | −4.6983 | 0.3000 | 1.51633 | 64.14 |
| 7 | 4.6936 | 0.1025 | | |
| 8 | 2.1908 | 0.7300 | 1.69680 | 55.53 |
| 9 | −15.9753 | 0.1000 | | |
| 10* | −13.1672 | 0.3000 | 1.85026 | 32.27 |
| 11 | 4.0126 | 0.9500 | 1.49700 | 81.54 |
| 12 | −2.0357 | 0.1000 | | |
| 13 | −1.1309 | 0.2100 | 1.95906 | 17.47 |
| 14 | 1.5997 | 0.3600 | 1.48749 | 70.23 |
| 15 | −1.3908 | 0.1000 | | |

-continued

Unit mm

| | | | | |
|---|---|---|---|---|
| 16 | ∞ | 0.2200 | 1.80610 | 40.92 |
| 17 | 1.5184 | 0.3700 | 1.80518 | 25.42 |
| 18 | −1.4145 | 0.0500 | | |
| 19 (Stop) | ∞ | d1 | | |
| 20 | ∞ | 0.3100 | 1.80518 | 25.42 |
| 21 | −6.1791 | 0.2400 | 1.53172 | 48.84 |
| 22 | 1.9254 | d2 | | |
| 23 | 1.4918 | 0.3900 | 2.00330 | 28.27 |
| 24 | 7.1660 | 0.0500 | | |
| 25 | 1.3286 | 0.3300 | 1.77250 | 49.60 |
| 26 | ∞ | 0.2300 | 1.80518 | 25.42 |
| 27 | 1.4096 | 0.1300 | | |
| 28 | −18.3946 | 0.2100 | 1.95906 | 17.47 |
| 29 | 0.5534 | 0.5600 | 1.48749 | 70.23 |
| 30 | −1.2753 | 0.1000 | | |
| 31 | ∞ | 0.4500 | 1.51633 | 64.14 |
| 32 | ∞ | 0.0100 | 1.51300 | 64.00 |
| 33 | ∞ | 0.3500 | 1.50510 | 63.26 |
| 34 | ∞ | 0.0006 | | |
| Image plane | ∞ | | | |

Aspherical surface data

6th surface k = −1.0541
A4 = −4.4267E-02, A6 = 6.8814E-03, A8 = 3.0686E-03

10th surface k = −0.2974
A4 = −2.3416E-02, A6 = −7.5181E-03

Various data

| IH | 0.48 |
|---|---|
| φ | 0.74 |
| L | 1.4 |

| | far-point observation | near-point observation |
|---|---|---|
| NA | 0.00776 | 0.02563 |
| ΔI | 0.01399 | 0.05364 |
| d0 | 10 | 2 |
| d1 | 0.19277 | 0.8 |
| d2 | 0.65723 | 0.05 |

Example 4

Unit mm
Surface data

| Surface no. | r | d | nd | vd |
|---|---|---|---|---|
| Object plane | ∞ | d0 | | |
| 1 | ∞ | 0.3000 | 1.88300 | 40.76 |
| 2 | 2.7003 | 0.6100 | | |
| 3 | −2.4659 | 0.3000 | 1.81600 | 46.62 |
| 4 | 2.7009 | 0.6100 | 1.92286 | 18.90 |
| 5 | −18.5670 | 0.1500 | | |
| 6* | −4.6983 | 0.3000 | 1.51633 | 64.14 |
| 7 | 4.6936 | 0.1025 | | |
| 8 | 2.1908 | 0.7300 | 1.69680 | 55.53 |
| 9 | −15.9753 | 0.1000 | | |
| 10* | −13.1672 | 0.3000 | 1.85026 | 32.27 |
| 11 | 4.0126 | 0.9500 | 1.49700 | 81.54 |
| 12 | −2.0357 | 0.2000 | | |
| 13 | −1.2746 | 0.2100 | 1.95906 | 17.47 |
| 14 | 0.7836 | 0.3600 | 1.48749 | 70.23 |
| 15 | −1.6364 | 0.1000 | | |
| 16 | ∞ | 0.2400 | 1.81600 | 46.62 |
| 17 | 1.5793 | 0.4900 | 1.84666 | 23.78 |

-continued

Unit mm

| | | | | |
|---|---|---|---|---|
| 18 | −1.1918 | 0.0500 | | |
| 19 (Stop) | ∞ | d1 | | |
| 20 | ∞ | 0.4100 | 1.81600 | 46.62 |
| 21 | −3.3553 | 0.2400 | 1.71736 | 29.52 |
| 22 | 1.6881 | d2 | | |
| 23 | 1.5758 | 0.4900 | 2.00330 | 28.27 |
| 24 | 3.4809 | 0.1000 | | |
| 25 | 1.2152 | 0.5800 | 1.72916 | 54.68 |
| 26 | −28.0805 | 0.2800 | 1.84666 | 23.78 |
| 27 | 16.1478 | 0.1300 | | |
| 28 | −1.9818 | 0.2100 | 1.92286 | 18.90 |
| 29 | 0.5602 | 0.5600 | 1.48749 | 70.23 |
| 30 | −1.2459 | 0.1180 | | |
| 31 | ∞ | 0.4500 | 1.51633 | 64.14 |
| 32 | ∞ | 0.0100 | 1.51300 | 64.00 |
| 33 | ∞ | 0.3500 | 1.50510 | 63.26 |
| 34 | ∞ | −0.0001 | | |
| Image plane | ∞ | | | |

Aspherical surface data

6th surface k = −1.0541
A4 = −4.4267E-02, A6 = 6.8814E-03, A8 = 3.0686E-03

10th surface k = −0.2974
A4 = −2.3416E-02, A6 = −7.5181E-03

Various data

| IH | 0.48 |
|---|---|
| φ | 0.74 |
| L | 1.4 |

| | far-point observation | near-point observation |
|---|---|---|
| NA | 0.0041 | 0.02526 |
| ΔI | 0.0079 | 0.0551 |
| d0 | 20 | 2 |
| d1 | 0.08 | 0.495 |
| d2 | 0.485 | 0.05 |

Example 5

Unit mm
Surface data

| Surface no. | r | d | nd | vd |
|---|---|---|---|---|
| Object plane | ∞ | d0 | | |
| 1 | ∞ | 0.3000 | 1.88300 | 40.76 |
| 2 | 5.0431 | 0.4300 | | |
| 3 | −4.6915 | 0.3000 | 1.74100 | 52.64 |
| 4 | 4.9455 | 0.6100 | 1.92286 | 18.90 |
| 5 | 130.4245 | 0.3800 | | |
| 6 | −1.8638 | 0.3000 | 1.48749 | 70.23 |
| 7 | 2.3779 | 0.4105 | | |
| 8 | 4.3309 | 0.7300 | 1.69680 | 55.53 |
| 9 | −3.8769 | 0.1000 | | |
| 10 | 33.9260 | 0.3000 | 1.85026 | 32.27 |
| 11 | 3.3817 | 0.9500 | 1.49700 | 81.54 |
| 12 | −2.6859 | 0.1200 | | |
| 13 | −1.3145 | 0.2100 | 2.00330 | 28.27 |
| 14 | 0.6756 | 0.4100 | 1.51633 | 64.14 |
| 15 | −1.8029 | 0.1000 | | |
| 16 | ∞ | 0.2400 | 1.84666 | 23.78 |
| 17 | 7.9287 | 0.4900 | 1.80610 | 40.92 |
| 18 | −1.1000 | 0.0500 | | |
| 19(Stop) | ∞ | d1 | | |
| 20 | ∞ | 0.3200 | 1.49700 | 81.54 |

-continued

Unit mm
Surface data

| | | | | |
|---|---|---|---|---|
| 21 | 1.1309 | 0.3300 | 1.84666 | 23.78 |
| 22 | 1.2208 | d2 | | |
| 23 | 1.7338 | 0.7000 | 1.48749 | 70.23 |
| 24 | −7.4321 | 0.1000 | | |
| 25 | 1.8975 | 0.6000 | 1.49700 | 81.54 |
| 26 | ∞ | 0.1300 | | |
| 27 | 1.2646 | 0.5100 | 1.51633 | 64.14 |
| 28 | 9.4761 | 0.3000 | 1.95906 | 17.47 |
| 29 | 0.7000 | 0.3400 | | |
| 30 | 3.1035 | 0.4500 | 1.51633 | 64.14 |
| 31 | ∞ | 0.0100 | 1.51300 | 64.00 |
| 32 | ∞ | 0.3500 | 1.50510 | 63.26 |
| 33 | ∞ | 0.0000 | | |
| Image plane | ∞ | | | |

Various data

| | | |
|---|---|---|
| IH | | 0.45 |
| φ | | 0.8 |
| L | | 0.7 |

| | far-point observation | near-point observation |
|---|---|---|
| NA | 0.00663 | 0.02061 |
| ΔI | 0.01399 | 0.05266 |
| d0 | 10 | 2 |
| d1 | 0.11969 | 0.465 |
| d2 | 0.53031 | 0.185 |

Next, values of conditional expressions in each example are given below. '-' (hyphen) indicates that there is no corresponding arrangement. With respect to Example 2 to Example 5, two values are described in the conditional expression (1). A value of an upper column indicates a value at a time of the far-point observation, and a value of a lower column indicates a value at a time of the near-point observation.

| | Example1 | Example2 | Example3 |
|---|---|---|---|
| (1)-f21n/fSUB | 1.908 | 1.694 | 0.889 |
| | | 1.908 | 0.973 |
| (2)-L × f1/f2 | 0.56 | 0.56 | 0.56 |
| (3)f22R1/f22R | 0.855 | 0.855 | 0.81 |
| (4)-f21n/f21p | 1.101 | 1.101 | — |
| (4')-f21n/f21p | — | — | 0.827 |

| | Example4 | Example5 |
|---|---|---|
| (1)-f21n/fSUB | 0.609 | 0.551 |
| | 0.678 | 0.623 |
| (2)-L × f1/f2 | 0.56 | 0.56 |
| (3)f22R1/f22R | 1.453 | 1.7 |
| (4)-f21n/f21p | — | — |
| (4')-f21n/f21p | 0.741 | 0.654 |

Figure 12:
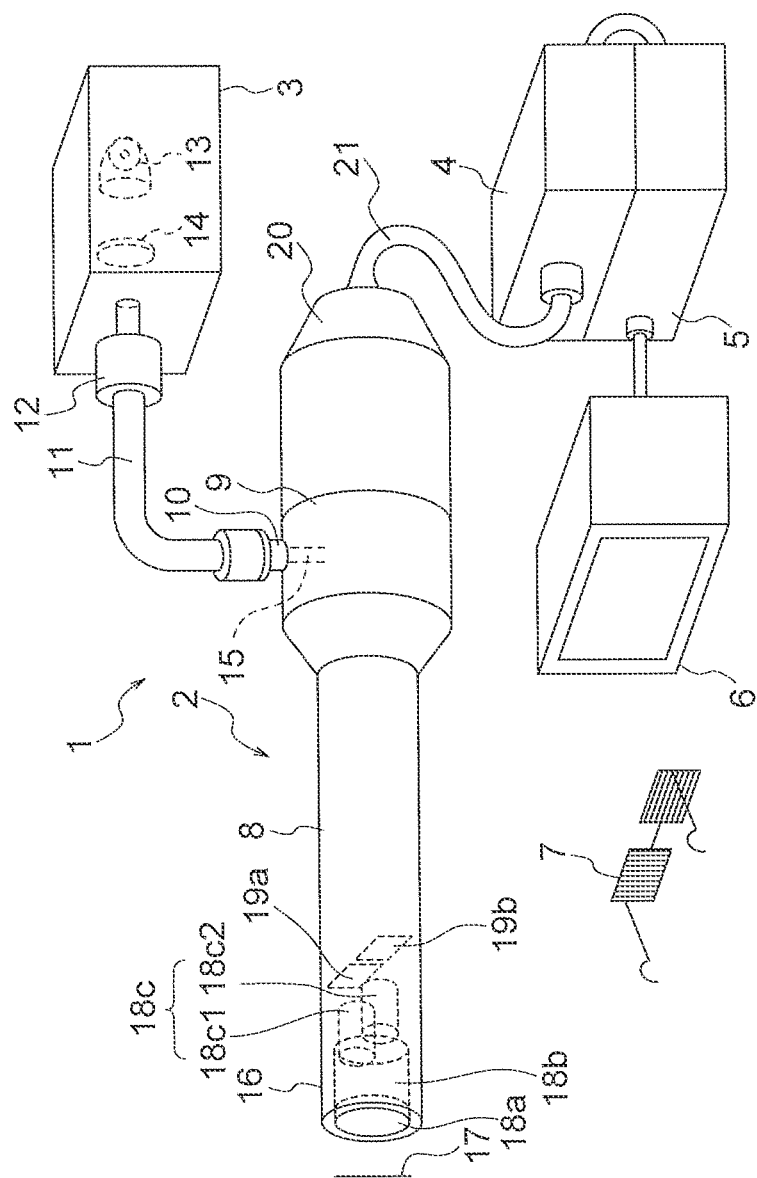
FIG. 12 is a diagram showing an endoscope of the present embodiment.

FIG. 12 is a diagram showing an endoscope of the present embodiment. The endoscope of the present embodiment is a stereoscopic-vision endoscope. A stereoscopic-vision endoscope 1 includes a body portion 2, a light-source unit 3, a camera control unit 4 (hereinafter, referred to as 'CCU 4'), a scan converter 5, a monitor 6, and shutter glasses 7.

The body portion 2 includes an insertion portion 8 and a holding portion 9. The insertion portion 8 is a portion to be inserted into a body cavity, and is formed by a hard jacket tube. The jacket tube is in the form of a circular tube, and is made of a metal such as stainless steel. In such manner, the stereoscopic-vision endoscope 1 is a rigid endoscope. The holding portion 9 is a portion to be held by an operator.

The holding portion 9 is provided with a light-guide tube 10. One end of a light-guide cable 11 is connected to the light-guide tube 10. The other end of the light-guide cable 11 is provided with a light-guide connector 12. The light-guide cable 11 is detachably connected to the holding portion 9 and the light-source unit 3.

The light-source unit 3 includes a lamp 13 and a lens 14. The lamp 13 generates illumination light such as white light. The lens 14 focuses the illumination light. The illumination light focused by the lens 14 is irradiated to an end surface of the light-guide connector 12. The illumination light irradiated to the end surface is transmitted to the body portion 2 by a light guide inside the light-guide cable 11.

The body portion 2 is provided with a light guide 15. The light guide 15 is bent inside the holding portion 9, and is passed through the insertion portion 8. The light guide 15 transmits the illumination light supplied from the light-guide cable 11 to a front-end surface which is fixed to a front-end portion 16 of the insertion portion 8. Accordingly, the illumination light is emerged frontward from the front-end surface.

Inside of the front-end portion 16, a stereoscopic vision optical system of the present embodiment is disposed. The stereoscopic vision optical system includes a first lens group 18a, a second lens group 18b, and a rear-side lens group 18c. The rear-side lens group 18c includes a first rear group 18c1 and a second rear group 18c2.

An object 17 is illuminated by the illumination light. Light from the object 17 is incident on the first lens group 18a and the second lens group 18b. Light emerged from the second lens group 18b is incident on the first rear group 18c1, and thereby a first optical image is formed at an image forming position. Light emerged from the second lens group 18b is incident on the second rear group 18c2, and thereby a second optical image is formed at an image forming position.

The first optical image and the second optical image are formed same region. Therefore, when the first optical image and the second optical image are captured, one image sensor or two image sensor may be used. In the stereoscopic-vision endoscope 1, an image sensor 19a and an image sensor 19b are disposed on the image forming position.

One end of a signal cable 21 is connected to an output portion 20. The other end of the signal cable 21 is connected to the CCU 4. A signal which is output from the image sensor 19 is input to the CCU 4 via the signal cable 21.

In the CCU 4, signal processing is carried out on signals output from the image sensor 19. An image signal subjected to signal processing in the CCU 4 is input to the scan converter 5. In the scan converter 5, the signal output from the CCU 4 is converted to a video signal.

The video signal is input to the monitor 6. The monitor 6 displays the video signal that has been input. Two images having a parallax are displayed alternately on the monitor 6. The shutter glasses 7 have a shutter function. By using the shutter glasses 7, images displayed on the monitor 6 can be viewed stereoscopically.

(Note)

A disclosure of the following arrangements is derived from the examples described above.

APPENDED MODE 1

The stereoscopic vision endoscope objective optical system, wherein a negative lens having the smallest negative refractive power is located nearest to an image, in the first lens group.

APPENDED MODE 2

The stereoscopic vision endoscope objective optical system, wherein the first lens group includes four lenses.

APPENDED MODE 3

The stereoscopic vision endoscope objective optical system, wherein a distance between an entrance pupil of the first rear group and an entrance pupil of the second rear group is in a range of 0.4 mm to 4 mm. The stereoscopic vision endoscope objective optical system, wherein the distance between the entrance pupil of the first rear group and the entrance pupil of the second rear group is in a range of 0.7 mm to 1 mm.

APPENDED MODE 4

The stereoscopic vision endoscope objective optical system, wherein a distance between an aperture stop in the second rear group and an aperture stop in the first rear group (distance between the entrance pupils) viewed from a side of incidence of the first lens is in a range of 0.2 mm to 1.6 mm. And preferably the distance between the entrance pupils is in a range of 0.35 mm to 1.0 mm.

According to the present disclosure, it is possible to provide a small-size stereoscopic vision endoscope objective optical system having a wide angle of view, which enables to achieve an appropriate stereoscopic effect, and an endoscope using the stereoscopic vision endoscope objective optical system.

As described heretofore, the present disclosure is suitable for a small-size stereoscopic vision endoscope objective optical system having a wide angle of view, which enables to achieve an appropriate stereoscopic effect, and an endoscope using the stereoscopic vision endoscope objective optical system.

What is claimed is:

1. A stereoscopic vision endoscope objective optical system comprising, in order from an object side:
    a first lens group having a negative refractive power;
    a second lens group having a positive refractive power; and
    a rear-side lens group having a positive refractive power, wherein:
    the rear-side lens group includes a first rear group and a second rear group,
    the first lens group and the second lens group are disposed so that an optical axis of the second lens group coincides with an optical axis of the first lens group,
    the optical axis of the first lens group is located between an optical axis of the first rear group and an optical axis of the second rear group,
    each of the first rear group and the second rear group includes a first sub group, an aperture stop, and a second sub group,
    the first sub group has a positive refractive power and includes, in order from the object side, a negative lens and a positive lens, and
    the following conditional expressions (1) and (2) are satisfied:

$$0 < -f21n/fSUB \leq 3 \qquad (1)$$

$$0.2 \text{ mm} \leq -L \times f1/f2 \leq 2 \text{ mm} \qquad (2)$$

where,
    $f21n$ denotes a focal length of the negative lens in the first sub group,
    $fSUB$ denotes a focal length of the first rear group or a focal length of the second rear group,
    $L$ denotes a distance between the optical axis of the first rear group and the optical axis of the second rear group,
    $f1$ denotes a focal length of the first lens group, and
    $f2$ denotes a focal length of the second lens group.

2. The stereoscopic vision endoscope objective optical system according to claim 1, wherein:
    the second sub group includes a front-side sub group having a negative refractive power and a rear-side sub group having a positive refractive power, and
    focusing is carried out by moving the front-side sub group along its optical axis.

3. The stereoscopic vision endoscope objective optical system according to claim 2, wherein:
    a positive lens is located nearest to an object in the rear-side sub group, and
    the following conditional expression (3) is satisfied:

$$0.6 \leq f22R1/f22R \leq 1.9 \qquad (3)$$

where,
    $f22R1$ denotes a focal length of the positive lens in the rear-side sub group, and
    $f22R$ denotes a focal length of the rear-side sub group.

4. The stereoscopic vision endoscope objective optical system according to claim 3, wherein:
    the rear-side sub group in the second sub group includes, in order from the object side, a positive lens, a negative lens, and a positive lens, and
    the following conditional expression (4) is satisfied:

$$0.9 \leq -f21n/f21p \leq 1.5 \qquad (4)$$

where,
    $f21p$ denotes a focal length of the positive lens in the first sub group.

5. The stereoscopic vision endoscope objective optical system according to claim 1, wherein:
    the second sub group includes a front-side sub group having a negative refractive power and a rear-side sub group having a positive refractive power,
    the rear-side sub group in the second sub group includes, in order from the object side, a positive lens, a negative lens, and a positive lens, and
    the following conditional expression (4) is satisfied:

$$0.9 \leq -f21n/f21p \leq 1.5 \qquad (4)$$

where,
    $f21p$ denotes a focal length of the positive lens in the first sub group.

6. The stereoscopic vision endoscope objective optical system according to claim 1, wherein each of the first rear group and the second rear group includes, in order from the object side, the first sub group, the aperture stop, and the second sub group.

7. An endoscope comprising:
    the stereoscopic vision endoscope objective optical system according to claim 1; and
    an image sensor which captures an optical image formed by the stereoscopic vision endoscope objective optical system.

8. A stereoscopic vision endoscope objective optical system comprising, in order from an object side:
    a first lens group having a negative refractive power;
    a second lens group having a positive refractive power; and
    a rear-side lens group having a positive refractive power, wherein:

the rear-side lens group includes a first rear group and a second rear group, the first lens group and the second lens group are disposed so that an optical axis of the second lens group coincides with an optical axis of the first lens group, the optical axis of the first lens group is located between an optical axis of the first rear group and an optical axis of the second rear group, each of the first rear group and the second rear group includes a first sub group, an aperture stop, and a second sub group, the first sub group includes, in order from the object side, a negative lens and a positive lens, the second sub group includes a front-side sub group having a negative refractive power and a rear-side sub group having a positive refractive power, focusing is carried out by moving the front-side sub group along its optical axis, the rear-side sub group in the second sub group includes, in order from the object side, a positive lens, a positive lens, and a negative lens, and the following conditional expressions (1) and (4') are satisfied:

$$0 < -f21n/fSUB \leq 3 \quad (1)$$

$$0.5 \leq -f21n/f21p \leq 1 \quad (4')$$

where, f21n denotes a focal length of the negative lens in the first sub group, fSUB denotes a focal length of the first rear group or a focal length of the second rear group, and f21p denotes a focal length of the positive lens in the first sub group.

9. A stereoscopic vision endoscope objective optical system comprising, in order from an object side:

a first lens group having a negative refractive power;

a second lens group having a positive refractive power; and a rear-side lens group having a positive refractive power, wherein:

the rear-side lens group includes a first rear group and a second rear group, the first lens group and the second lens group are disposed so that an optical axis of the second lens group coincides with an optical axis of the first lens group, the optical axis of the first lens group is located between an optical axis of the first rear group and an optical axis of the second rear group, each of the first rear group and the second rear group includes a first sub group, an aperture stop, and a second sub group, the first sub group includes, in order from the object side, a negative lens and a positive lens, the second sub group includes a front-side sub group having a negative refractive power and a rear-side sub group having a positive refractive power, the rear-side sub group in the second sub group includes, in order from the object side, a positive lens, a positive lens, and a negative lens, and the following conditional expressions (1) and (4') are satisfied:

$$0 < -f21n/fSUB \leq 3 \quad (1)$$

$$0.5 \leq -f21n/f21p \leq 1 \quad (4')$$

where, f21n denotes a focal length of the negative lens in the first sub group, fSUB denotes a focal length of the first rear group or a focal length of the second rear group, and f21p denotes a focal length of the positive lens in the first sub group.

* * * * *